United States Patent
Aoki

(10) Patent No.: US 10,190,997 B2
(45) Date of Patent: Jan. 29, 2019

(54) X-RAY DEVICE, METHOD, MANUFACTURING METHOD FOR STRUCTURE, PROGRAM, AND RECORDING MEDIUM ON WHICH PROGRAM IS RECORDED

(71) Applicant: NIKON CORPORATION, Tokyo (JP)

(72) Inventor: Takashi Aoki, Sagamihara (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 14/332,942

(22) Filed: Jul. 16, 2014

(65) Prior Publication Data
US 2015/0010127 A1 Jan. 8, 2015

Related U.S. Application Data

(63) Continuation of application No. PCT/JP2013/050959, filed on Jan. 18, 2013.

(30) Foreign Application Priority Data

Jan. 20, 2012 (JP) ................................ 2012-010370

(51) Int. Cl.
*G01N 23/04* (2018.01)
*G01N 23/083* (2018.01)
(Continued)

(52) U.S. Cl.
CPC ......... *G01N 23/083* (2013.01); *G01N 23/087* (2013.01); *G05B 15/02* (2013.01);
(Continued)

(58) Field of Classification Search
CPC ....... G01N 2223/306; G01N 2223/401; G01N 2223/402; G01N 2223/615;
(Continued)

(56) References Cited

U.S. PATENT DOCUMENTS 6,088,423 A * 7/2000 Krug et al. .......... G01V 5/0016
7,813,470 B2 * 10/2010 Kuwabara ............ G01N 23/087
(Continued)

FOREIGN PATENT DOCUMENTS

JP 61-98242 5/1986
JP 2011-24773 A 2/2011

OTHER PUBLICATIONS

Preliminary Examination Report issued by the Intellectual Property Office of Taiwan in counterpart Taiwanese Patent Application No. 102102172, dated Sep. 2, 2015, 17 pages.
(Continued)

*Primary Examiner* — Thomas R Artman
(74) *Attorney, Agent, or Firm* — Finnegan, Henderson, Farabow, Garrett & Dunner, LLP

(57) ABSTRACT

There is provided an X-ray device irradiating a measuring object with X-ray and detecting transmission X-ray transmitted through the measuring object, the X-ray device including: a first information generation portion configured to generate first information in which a value according to an absorption coefficient is allocated to each of a plurality of divided sections into which there is divided a predetermined space including at least part of the measuring object; a frequency generation portion configured to generate frequency information of the allocated value to indicate a number of the divided sections according to magnitude of the allocated value in the first information; a ratio acquirement portion configured to acquire ratio information indicating a ratio between a first substance and a second substance constituting the measuring object; and a second information generation portion configured to change the first information into second information, by using the frequency information and the ratio information.

25 Claims, 20 Drawing Sheets

(51) Int. Cl.
 G05B 15/02 (2006.01)
 G01N 23/087 (2018.01)
(52) U.S. Cl.
 CPC . G01N 2223/306 (2013.01); G01N 2223/401 (2013.01); G01N 2223/402 (2013.01); G01N 2223/405 (2013.01); G01N 2223/615 (2013.01); G01N 2223/623 (2013.01); G01N 2223/645 (2013.01)
(58) Field of Classification Search
 CPC ....... G01N 2223/623; G01N 2223/645; G01N 23/083; G01N 23/087; G01N 21/47; G01N 21/59; G01N 2201/021; G01N 2201/0612; G01N 2201/062; G01N 2223/419; G01N 23/046; G01N 23/00; G01N 2223/00; G05B 15/02; G01V 5/0016; G01V 5/00
 USPC .............................................. 378/4, 5, 9, 53
 See application file for complete search history.

(56) References Cited

U.S. PATENT DOCUMENTS

2002/0154728 A1  10/2002  Morita et al.
2009/0268889 A1  10/2009  Hadland
2010/0172470 A1   7/2010  Kuwabara
2010/0220908 A1   9/2010  Khare et al.
2011/0116605 A1*  5/2011  Radley ................ G01N 23/087
                                                378/162

OTHER PUBLICATIONS

First Examination Report of Chinese Patent Application No. 201380005382.0, dated Sep. 15, 2015, and its English translation (25 pages).
Notification of Reasons for Rejection issued by the Japanese Patent Office in counterpart Japanese Patent Application No. 2013-554361, dated Aug. 5, 2015.
Extended International Search Report issued by the Hague in European Application No. 13 73 8159, dated Jul. 10, 2015, 7 pages.
International Search Report issued by the Japanese Patent Office in International Application No. PCT/JP2013/050959, dated Mar. 19, 2013, 4 pages.
Written Opinion of the International Searching Authority issued by the Japanese Patent Office in International Application No. PCT/JP2013/050959, dated Mar. 19, 2013, 12 pages.
Taiwanese Final Office Action of Taiwanese Application No. 102102172, dated Jul. 22, 2016 including English translation (12 pages total).

* cited by examiner

Fig. 4
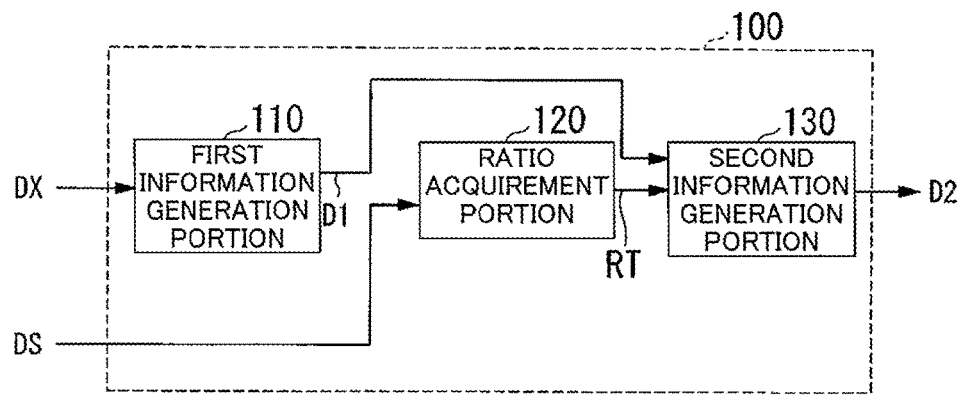
Fig. 5A
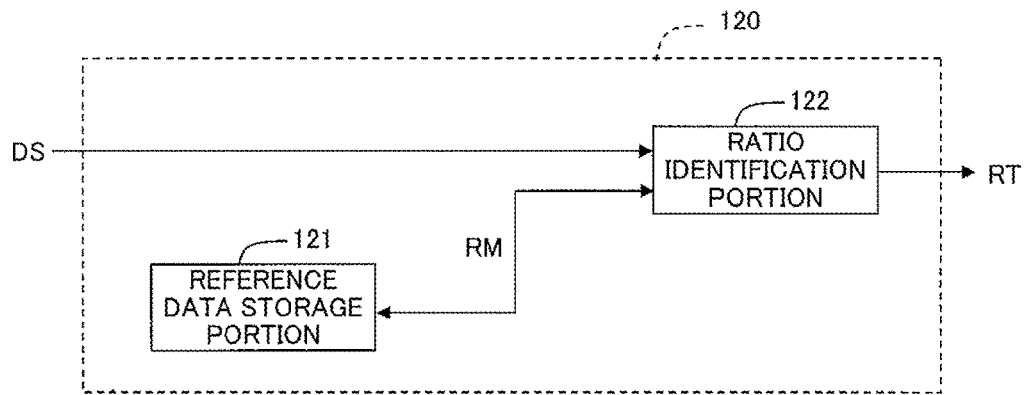
Fig. 5B
| COMBINATION OF SUBSTANCES | RATIO | WAVEFORM DATA |
|---|---|---|
| SUBSTANCE A + SUBSTANCE B | 4:1 | RM1 |
| SUBSTANCE A + SUBSTANCE C | 2:3 | RM2 |
| ... | ... | ... |

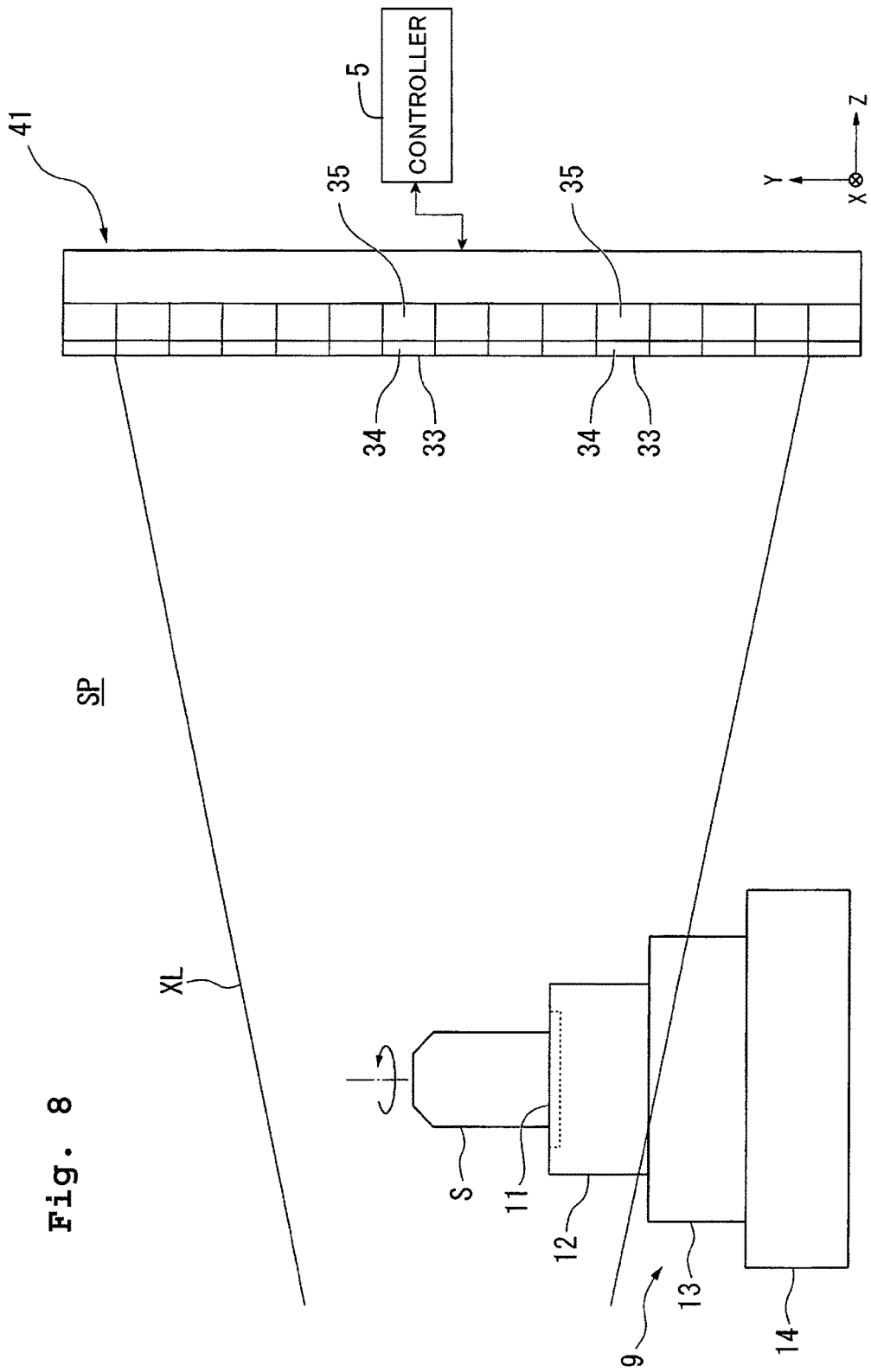

Fig. 19
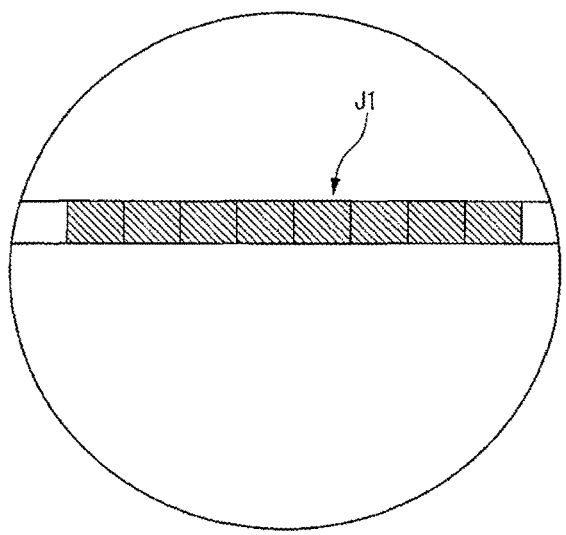
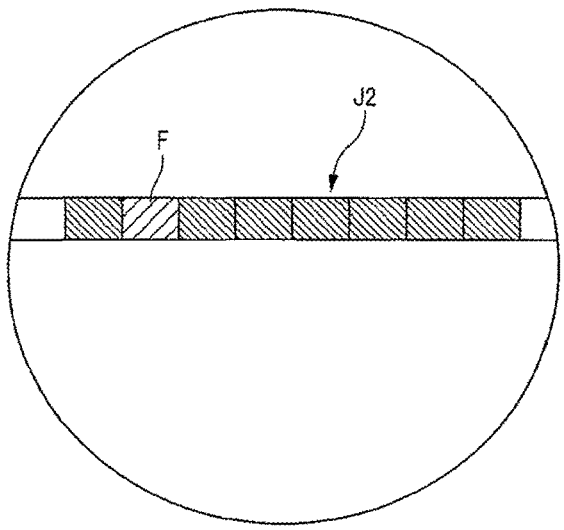

X-RAY DEVICE, METHOD, MANUFACTURING METHOD FOR STRUCTURE, PROGRAM, AND RECORDING MEDIUM ON WHICH PROGRAM IS RECORDED

CROSS REFERENCE TO RELATED APPLICATIONS

This is a continuation application of International Application No. PCT/JP2013/050959 filed on Jan. 18, 2013 which claims priority of Japanese Patent Application No. 2012-010370 filed on Jan. 20, 2012. The contents of the aforementioned applications are incorporated herein by reference in their entirety.

BACKGROUND

Field of the Invention

The present teaching relates to an X-ray device, a method, a manufacturing method for structure, a program, and a recording medium storing the program.

Description of the Related Art

As devices detecting a profile of an object, and an internal shape of the object, for example, such a device as disclosed in U.S. Patent Application Publication No. 2009/0268869 is known to irradiate the object with X-ray and detect transmission X-ray transmitted through that object.

SUMMARY

With conventional techniques of irradiating an object containing a plurality of types of materials or substances with X-ray, and detecting X-ray transmitted through the object, there are cases that some defection occurs in the results of detecting a profile of the object and an internal shape of the object, thereby causing defective detections.

An object of the present teaching is to provide an X-ray device, a method, and a manufacturing method for structure which are configured to restrain any defection of detecting a profile of an object and an internal shape of that object.

According to a first aspect of the present teaching, there is provided an X-ray device irradiating a measuring object with X-ray and detecting transmission X-ray transmitted through the measuring object, the X-ray device including: a first information generation portion configured to generate, by using a result of detecting the transmission X-ray, first information in which a value according to an absorption coefficient is allocated to each of a plurality of divided sections into which there is divided a predetermined space including at least part of the measuring object; a frequency generation portion configured to generate frequency information of the allocated value to indicate a number of the divided sections according to magnitude of the allocated value in the first information; a ratio acquirement portion configured to acquire ratio information indicating a ratio between a first substance and a second substance constituting the measuring object; and a second information generation portion configured to change the first information into second information, by using the frequency information and the ratio information.

According to a second aspect of the present teaching, there is provided a method including the steps of: irradiating a measuring object with X-ray, and detecting transmission X-ray transmitted through the measuring object; and generating second detection information from first detection information obtained by the detecting, according to a ratio between a first substance and a second substance contained in the measuring object.

According to a third aspect of the present teaching, there is provided a manufacturing method for structure, including: a design step of creating design information with respect to a profile of a structure; a formation step of fabricating the structure based on the design information; a measuring step of measuring the profile of the fabricated structure by using either the X-ray device according to the first aspect or the method according to the second aspect; and an inspection step of comparing information of the profile obtained in the measuring step with the design information.

According to a fourth aspect of the present teaching, there is provided a computer program configured to cause a computer connected to an X-ray device to carry out a control of the X-ray device, the computer program including instructions for controlling the X-ray device to carry out the steps of: irradiating a measuring object with X-ray, and detecting transmission X-ray transmitted through the measuring object; generating, by using a result of detecting the transmission X-ray, first information in which a value according to an absorption coefficient is allocated to each of a plurality of divided sections into which there is divided a predetermined space including at least part of the measuring object; generating frequency information of the allocated value to indicate a number of the divided sections according to magnitude of the allocated value in the first information; acquiring ratio information indicating a ratio between a first substance and a second substance constituting the measuring object; and changing the first information into second information, by using the frequency information and the ratio information.

According to a fifth aspect of the present teaching, there is provided a computer-readable recording medium storing the computer program according to the fourth aspect of the present teaching.

According to the above aspects of the present teaching, it is possible to restrain any defection of detecting a profile of an object and an internal shape of that object.

BRIEF DESCRIPTION OF THE DRAWINGS

FIG. 4 is a diagram showing an example of an information processing portion included in the X-ray device in accordance with the first embodiment;

FIG. 5A is a diagram showing an example of a ratio acquirement portion included in the information processing portion in accordance with the first embodiment;

FIG. 5B is a table showing an example of a reference data stored in the ratio acquirement portion in accordance with the first embodiment;

FIG. 8 is a view for explaining an example of operations of the X-ray device in accordance with the first embodiment;

FIG. 19 is a view for explaining an example of operation of the X-ray device in accordance with a fourth embodiment;

DESCRIPTION OF EMBODIMENTS

Embodiments of the present teaching will be explained hereinbelow with reference to the accompanying drawings. However, the present teaching is not limited to these embodiments. In the following explanations, an X-Y-Z orthogonal coordinate system is set up, and positional relations between respective parts are explained in reference to this X-Y-Z orthogonal coordinate system. A predetermined direction within a horizontal plane is defined as a Z-axis direction, a direction orthogonal to the Z-axis direction within the horizontal plane is defined as an X-axis direction, and a direction orthogonal respectively to the Z-axis direction and the X-axis direction (namely a vertical direction) is defined as a Y-axis direction. Further, the rotational (inclinational) directions about the X-axis the Y-axis and the Z-axis are defined as a θX direction, a θY direction and a θZ direction, respectively.

First Embodiment

A first embodiment will be explained.

Figure 1:
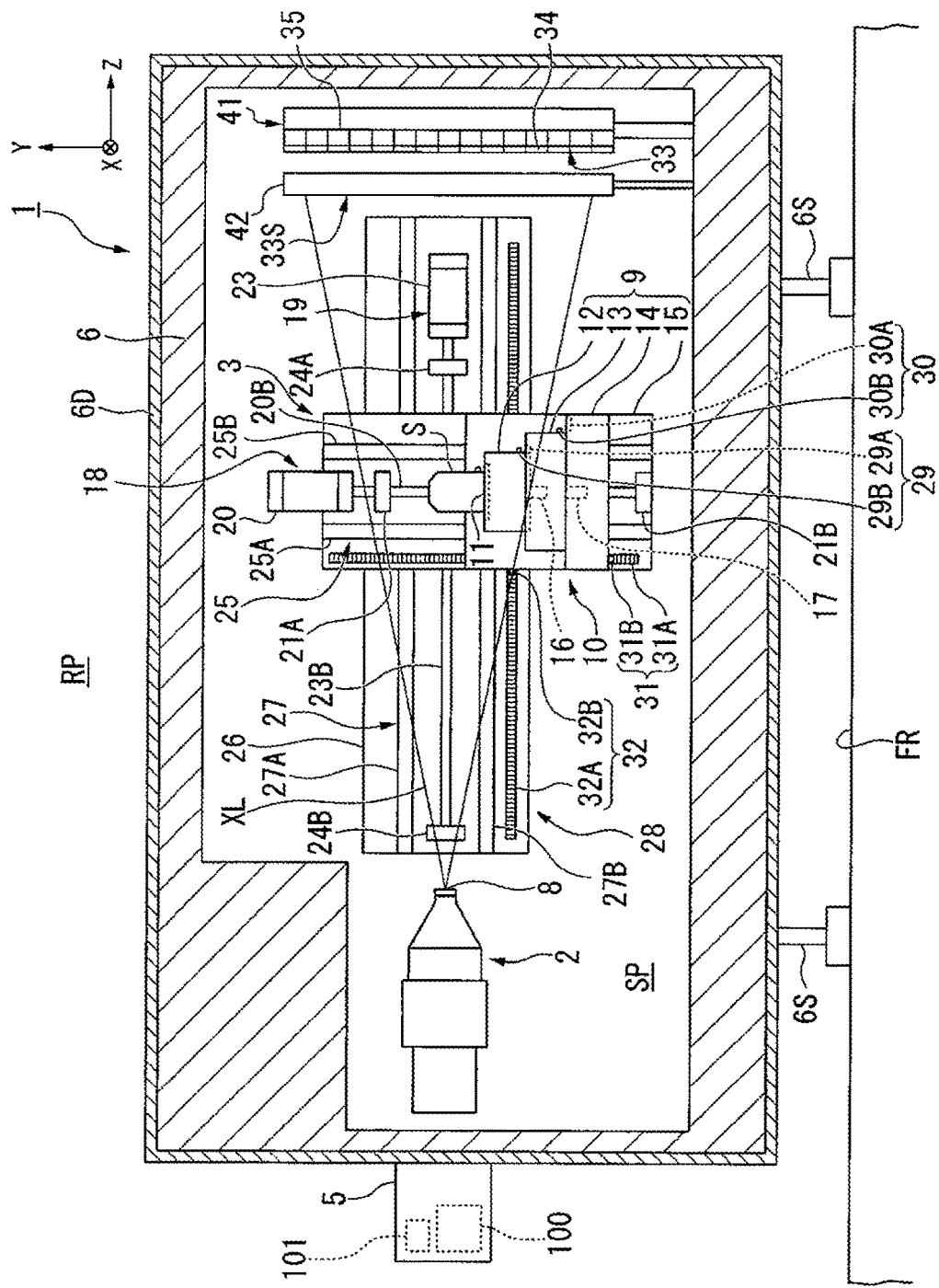
FIG. 1 is a view showing an example of an X-ray device in accordance with a first embodiment.

FIG. 1 is a view showing an example of an X-ray device 1 in accordance with the first embodiment.

The X-ray device 1 irradiates a measuring object S with X-ray XL to detect transmission X-ray transmitted through the measuring object S. The X-ray is, for example, an electromagnetic wave with a wavelength of approximately 1 pm to 30 nm. The X-ray includes at least one of ultrasoft X-ray at approximately 50 eV, soft X-ray at approximately 0.1 to 2 keV, X-ray at approximately 2 to 20 keV, and hard X-ray at approximately 20 to 100 keV.

In the first embodiment, the measuring object S contains a plurality of types of substances or materials. In the first embodiment, for the convenience of explanation, the measuring object S is considered to contain two types of substances: a first substance and a second substance and, for example, the first substance is lead and the second substance is iron. However, without being limited to this example, the first substance and the second substance may be any substances as long as they are different types of substances, and any number of types of substances is possible. Further, although different types of substances may be defined as substances with different X-ray absorption coefficients, for example, they are not limited to this example.

In the first embodiment, the X-ray device 1 includes an X-ray CT detection apparatus irradiating the measuring object S with the X-ray and detecting a transmission X-ray transmitted through the measuring object S so as to nondestructively acquire internal information of the measuring object S (an internal structure, for example). In the first embodiment, the measuring object S encompasses components for industrial use such as mechanical components, electronic components, and the like. The X-ray CT detection apparatus encompasses industrial X-ray CT detection apparatuses which irradiate the components for industrial use with the X-ray to inspect the components for industrial use.

In FIG. 1, the X-ray device 1 includes an X-ray source 2 emitting the X-ray XL, a movable stage device 3 retaining the measuring object S, a detection apparatus 41 detecting the transmission X-ray emitted from the X-ray source 2 and transmitted through the measuring object S retained by the stage device 3, a detection portion 42 (a detection unit, a detection member, or a detection mechanism) detecting the ratio ($I/I_0$) between an intensity $I_0$ of the X-ray irradiating the measuring object S and an intensity of the transmission X-ray transmitted through the measuring object S at each energy level of the X-ray, and a control device 5 controlling the operation of the whole X-ray device 1. In the first embodiment, the detection portion 42 is, for example, a spectrometer. Although the detection portion 42 is considered to be a spectrometer in the following description, the detection portion 42 is not limited to spectrometers.

Further, in the first embodiment, the X-ray device 1 includes a chamber member 6 defining an internal space SP where the X-ray XL emitted from the X-ray source 2 proceeds. In the first embodiment, the X-ray source 2, stage device 3, and detection apparatus 4 are arranged in the internal space SP.

In the first embodiment, the chamber member 6 is arranged over a support surface FR. The support surface FR encompasses floor surfaces in a factory or the like. The chamber member 6 is supported by a plurality of support members 6S. The chamber member 6 is arranged over the support surface FR via the support members 6S. In the first embodiment, the support members 6S separate the lower surface of the chamber member 6 from the support surface FR. That is, an interspace is formed between the lower surface of the chamber member 6 and the support surface FR. Further, it is also possible for at least part of the lower surface of the chamber member 6 to contact with the support surface FR.

In the first embodiment, the chamber member 6 contains lead. The chamber member 6 restrains the X-ray XL in the internal space SP from leaking out into an external space RP of the chamber member 6.

In the first embodiment, the X-ray device 1 has a member 6D which is fitted on the chamber member 6 and has a lower thermal conductivity than the chamber member 6. In the first embodiment, the member 6D is arranged on the external surface of the chamber member 6. The member 6D restrains the temperature of the internal space SP from being affected by the temperature (temperature change) of the external space RP. That is, the member 6D functions as a thermal insulation member restraining any heat in the external space RP from transferring into the internal space SP. The member 6D contains plastic, for example. In the first embodiment, the member 6D contains foamed polystyrene, for example.

The X-ray source 2 irradiates the measuring object S with the X-ray XL. The X-ray source 2 has an emission portion 8 (an emission unit, an emission mechanism, or an emission member) emitting the X-ray XL. The X-ray source 2 constitutes a point X-ray source. In the first embodiment, the emission portion 8 includes the point X-ray source. The X-ray source 2 irradiates the measuring object S with conical X-ray (a so-called cone beam). Further, the X-ray source 2 may be capable of adjusting the intensity of the emitting X-ray XL. Adjusting the intensity of the X-ray XL emitted from the X-ray source 2 may be based on the X-ray absorption feature and the like of the measuring object S. Further, the spreading shape of the X-ray emitted from the X-ray source 2 is not limited to a cone. For example, the X-ray may be fan-like X-ray (so-called fan beam). Further, for example, the X-ray may be linear X-ray (so-called pencil beam).

The emission portion 8 faces in the direction. In the first embodiment, at least part of the X-ray XL emitted from the emission portion 8 proceeds in the direction in the internal space SP.

The stage device 3 includes a movable stage 9 retaining the measuring object S, and a drive system 10 moving the stage 9.

In the first embodiment, the stage 9 has a table 12 having a retention portion 11 (a retention unit, a retention member, or a retention mechanism) retaining the measuring object S, a first movable member 13 movably supporting the table 12, a second movable member 14 movably supporting the first movable member 13, and a third movable member 15 movably supporting the second movable member 14.

The table 12 is rotatable with the measuring object S being retained by the retention portion 11. The table 12 is movable (rotatable) in the θY direction. The first movable member 13 is movable in the X-axis direction. If the first movable member 13 moves in the X-axis direction, then together with the first movable member 13, the table 12 also moves in the X-axis direction. The second movable member 14 is movable in the Y-axis direction. If the second movable member 14 moves in the Y-axis direction, then together with the second movable member 14, the first movable member 13 and the table 12 also move in the Y-axis direction. The third movable member 15 is movable in the Z-axis direction. If the third movable member 15 moves in the Z-axis direction, then together with the third movable member 15, the second movable member 14, the first movable member 13, and the table 12 also move in the Z-axis direction.

In the first embodiment, the drive system 10 includes a rotary drive device 16 rotating the table 12 on the first movable member 13, a first drive device 17 moving the first movable member 13 in the X-axis direction on the second movable member 14, a second drive device 18 moving the second movable member 14 in the Y-axis direction, and a third drive device 19 moving the third movable member 15 in the Z-axis direction.

The second drive device 18 includes a screw shaft 20B arranged in a nut of the second movable member 14, and an actuator 20 rotating the screw shaft 20B. The screw shaft 20B is rotatably supported by bearings 21A and 21B. In the first embodiment, the screw shaft 20B is supported by the bearings 21A and 21B such that the shaft line of the screw shaft 20B may become substantially parallel to the Y-axis. In the first embodiment, balls are arranged between the screw shaft 20B and the nut of the second movable member 14. That is, the second drive device 18 includes a so-called ball screw drive mechanism.

The third drive device 19 includes a screw shaft 23B arranged in a nut of the third movable member 15, and an actuator 23 rotating the screw shaft 23B. The screw shaft 23B is rotatably supported by bearings 24A and 24B. In the first embodiment, the screw shaft 23B is supported by the bearings 24A and 24B such that the shaft line of the screw shaft 23B may become substantially parallel to the Z-axis. In the first embodiment, balls are arranged between the screw shaft 23B and the nut of the third movable member 15. That is, the third drive device 19 includes another so-called ball screw drive mechanism.

The third movable member 15 has a guide mechanism 25 guiding the second movable member 14 in the Y-axis direction. The guide mechanism 25 includes guide members 25A and 25B elongated in the Y-axis direction. The third movable member 15 supports at least part of the second drive device 18 including the actuator 20, and the bearings 21A and 21B supporting the screw shaft 20B. By letting the actuator 20 rotate the screw shaft 20B, the second movable member 14 moves in the Y-axis direction while being guided by the guide mechanism 25.

In the first embodiment, the X-ray device 1 has a base member 26. The base member 26 is supported by the chamber member 6. In the first embodiment, the base member 26 is supported by the inner wall (internal surface) of the chamber member 6 via a support mechanism. The base member 26 is fixed in a predetermined position.

The base member 26 has a guide mechanism 27 guiding the third movable member 15 in the Z-axis direction. The guide mechanism 27 includes guide members 27A and 27B elongated in the Z-axis direction. The base member 26 supports at least part of the third drive device 19 including the actuator 23, and the bearings 24A and 24B supporting the screw shaft 23B. By letting the actuator 23 rotate the screw shaft 23B, the third movable member 15 moves in the Z-axis direction while being guided by the guide mechanism 27.

Further, while illustration is omitted, in the first embodiment, the second movable member 14 has a guide mechanism guiding the first movable member 13 in the X-axis direction. The first drive device 17 includes a ball screw mechanism capable of moving the first movable member 13 in the X-axis direction. The rotary drive device 16 includes a motor capable of moving (rotating) the table 12 in the θY direction.

In the first embodiment, by virtue of the drive system 10, the measuring object S retained on the table 12 is movable in four directions: the X-axis, Y-axis, Z-axis and θY directions. Further, it is also possible for the drive system 10 to move the measuring object S retained on the table 12 in six directions: the X-axis, Y-axis, Z-axis, θX, θY and θZ directions. Further, in the first embodiment, although the drive system 10 is contrived to include a ball screw drive mechanism, it may alternatively include, for example, a voice coil motor. Still alternatively, the drive system 10 may include, for example, a linear motor or a planar motor.

In the first embodiment, the stage 9 is movable in the internal space SP. The stage 9 is arranged on the +Z side of the emission portion 8. The stage 9 is movable in the space on the +Z side from the emission portion 8 within the internal space SP. At least part of the stage 9 can face the emission portion 8. The stage 9 can set the retained measuring object S to such a position as to face the emission portion 8. The stage 9 can set the measuring object S in such a path that the X-ray XL emitted from the emission portion 8 passes therethrough. The stage 9 can be arranged within the irradiation area of the X-ray XL emitted from the emission portion 8.

In the first embodiment, the X-ray device 1 includes a measuring system 28 which measures the position of the stage 9. In the first embodiment, the measuring system 28 includes an encoder system.

The measuring system 28 has a rotary encoder 29 measuring the rotational amount of the table 12 (the position with respect to the θY direction), a linear encoder 30 measuring the position of the first movable member 13 with respect to the X-axis direction, another linear encoder 31 measuring the position of the second movable member 14 with respect to the Y-axis direction, and still another linear encoder 32 measuring the position of the third movable member 15 with respect to the Z-axis direction.

In the first embodiment, the rotary encoder 29 measures the rotational amount of the table 12 relative to the first movable member 13. The linear encoder 30 measures the position of the first movable member 13 (the position with respect to the X-axis direction) relative to the second movable member 14. The linear encoder 31 measures the position of the second movable member 14 (the position with respect to the Y-axis direction) relative to the third movable member 15. The linear encoder 32 measures the position of the third movable member 15 (the position with respect to the Z-axis direction) relative to the base member 26.

The rotary encoder 29 includes, for example, a scale member 29A arranged on the first movable member 13, and an encoder head 29B arranged on the table 12 to detect the scale of the scale member 29A. The scale member 29A is fixed on the first movable member 13. The encoder head 29B is fixed on the table 12. The encoder head 29B can measure the rotational amount of the table 12 relative to the scale member 29A (the first movable member 13).

The linear encoder 30 includes, for example, a scale member 30A arranged on the second movable member 14, and an encoder head 30B arranged on the first movable member 13 to detect the scale of the scale member 30A. The scale member 30A is fixed on the second movable member 14. The encoder head 30B is fixed on the first movable member 13. The encoder head 30B can measure the position of the first movable member 13 relative to the scale member 30A (the second movable member 14).

The linear encoder 31 includes a scale member 31A arranged on the third movable member 15, and an encoder head 31B arranged on the second movable member 14 to detect the scale of the scale member 31A. The scale member 31A is fixed on the third movable member 15. The encoder head 31B is fixed on the second movable member 14. The encoder head 31B can measure the position of the second movable member 14 relative to the scale member 31A (the third movable member 15).

The linear encoder 32 includes a scale member 32A arranged on the base member 26, and an encoder head 32B arranged on the third movable member 15 to detect the scale of the scale member 32A. The scale member 32A is fixed on the base member 26. The encoder head 32B is fixed on the third movable member 15. The encoder head 32B can measure the position of the third movable member 15 relative to the scale member 32A (the base member 26).

The detection apparatus 41 and the detection portion 42 are arranged in the internal space SP on the +Z side from the X-ray source 2 and the stage 9. The detection apparatus 41 is fixed in a predetermined position. Alternatively, the detection apparatus 41 may be movable. The detection portion 42 is arranged on the −Z side from the detection apparatus 41. In the first embodiment, the detection portion 42 is arranged to be movable in the X-axis direction. The stage 9 is movable in the space between the X-ray source 2 and the detection apparatus 41 (or the detection portion 42) within the internal space SP.

In the first embodiment, the detection apparatus 41 has scintillator portions 34 (scintillator units, scintillator members, or scintillator mechanisms) having an incidence surface 33 on which the X-ray XL is incident, the X-ray coming from the X-ray source 2 and including the transmission X-ray transmitted through the measuring object S; and light receiving portions 35 (light receiving units, light receiving members, or light receiving mechanisms) respectively receiving light rays generated in the scintillator portions 34. The incidence surface 33 of the detection apparatus 41 can face the measuring object S retained on the stage 9.

Each of the scintillator portions 34 includes a scintillation substance which, by exposing itself to X-ray, generates a light ray with a different wavelength from that X-ray. Each of the light receiving portions 35 includes a photomultiplier tube. The photomultiplier tube includes a phototube converting optical energy into electrical energy by photoelectric effect. The light receiving portions 35 amplify the light rays generated in the scintillator portions 34, and convert the light rays into an electrical signal to output the latter.

The detection apparatus 41 has a plurality of the scintillator portions 34. The plurality of scintillator portions 34 are arranged within the X-Y plane. The scintillator portions 34 are arranged in an array-like form. The detection apparatus 41 has a plurality of the light receiving portions 35 to connect respectively with the plurality of scintillator portions 34. Further, it is also possible for the detection apparatus 41 to directly convert the incident X-ray into the electrical signal without first converting it into the light rays.

In the first embodiment, the detection portion 42 is arranged together with the detection apparatus 41 in the internal space SP of the chamber 6.

Figure 2A:
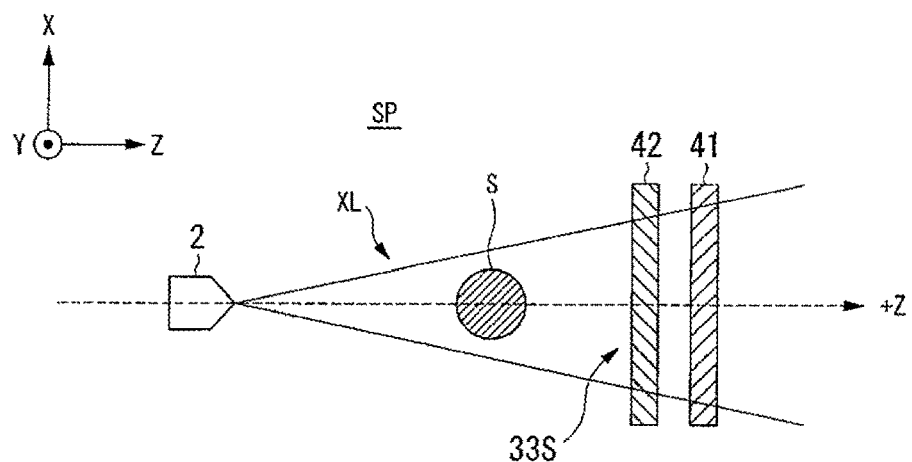
FIG. 2A is a view showing an example of arranging a detection portion of the X-ray device in accordance with the first embodiment.
Figure 2B:
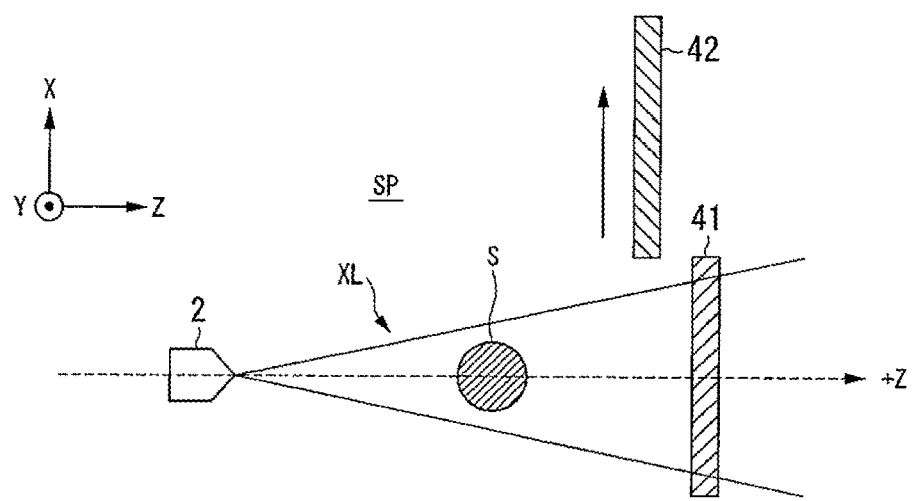
FIG. 2B is another view showing the example of arranging the detection portion of the X-ray device in accordance with the first embodiment.
Figure 3A:
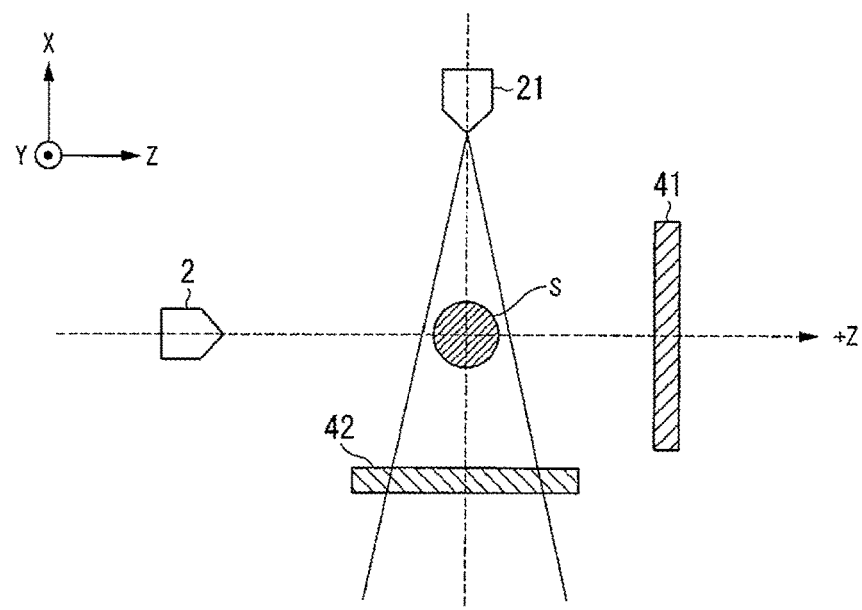
FIG. 3A is a view showing another example of arranging the detection portion of the X-ray device in accordance with the first embodiment.
Figure 3B:
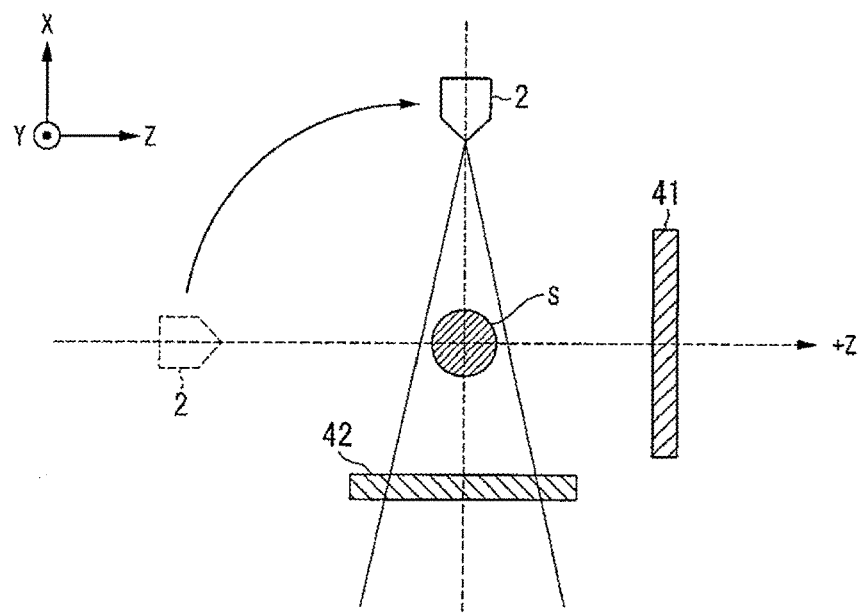
FIG. 3B is another view showing the other example of arranging the detection portion of the X-ray device in accordance with the first embodiment.

FIGS. 2A and 2B are views showing an example of arranging the detection apparatus 41 and detection portion 42 as the X-ray device 1 shown in FIG. 1 is observed from the Y-axis direction. Between the two views, FIG. 2A shows an example of arranging the X-ray source 2, detection apparatus 41, and detection portion 42 when the detection portion 42 detects the spectrum of the transmission X-ray transmitted through the measuring object S. FIG. 2B shows an example of arranging the X-ray source 2, detection apparatus 41, and detection portion 42 when the detection apparatus 41 detects the spectrum of the transmission X-ray transmitted through the measuring object S. Further, FIGS. 3A and 3B are views showing another example of arranging the detection apparatus 41 and detection portion 42, and showing the example in the case of radiating the X-ray from the X-axis direction and detecting the spectrum of the transmission X-ray. Between the two views, FIG. 3A shows an example of arranging an X-ray source 21 on the X-axis other than the X-ray source 2 on the Z-axis for radiating the X-ray in the X-axis direction. FIG. 3B shows an example of moving the X-ray source 2 on the Z-axis to the X-axis for radiating the X-ray in the X-axis direction.

As shown in FIG. 2A, the detection portion 42 is arranged in the internal space SF on the −Z side from the detection apparatus 41. Further, as shown in FIG. 2B, the detection portion 42 is movable in the X-axis direction. For the detection portion 42 to detect the spectrum of the transmission X-ray transmitted through the measuring object S, as shown in FIG. 2A, the detection portion 42 is arranged on the passage path of the X-ray XL, and arranged in a predetermined position on the −Z side from the detection apparatus 41. Further, for the detection apparatus 41 to detect the intensity of the transmission X-ray transmitted through the measuring object S, as shown in FIG. 2B, the detection portion 42 is moved from the abovementioned predetermined position shown in FIG. 2A to the +X side to be withdrawn from the passage path of the X-ray XL. The control device 5 controls the movement of the detection portion 42.

The arrangement of the detection apparatus 41 and detection portion 42 is not limited to the example shown in FIGS. 2A and 2B. For instance, in the example shown in FIGS. 2A and 2B, the position of the detection apparatus 41 and the position of the detection portion 42 may be exchanged to let the detection apparatus 41 be movable in the X-axis direction. Further, for example, the position of the detection apparatus 41 and the position of the detection portion 42 may be exchanged to let the detection portion 42 be movable in the X-axis direction.

Further, as shown in FIG. 3A, the X-ray source 21 different from the X-ray source 2 may be arranged on the +X side from the measuring object S, while the detection portion 42 may be arranged on the −X side from the measuring object S to face the X-ray source 21. In other words, along the X-axis, the X-ray source 21 different from the X-ray source 2 and the detection portion 42 may be arranged across the measuring object S. In the example shown in FIG. 3A, the relative position between the X-ray source 21, the measuring object S, and the detection portion 42 is the same as the aforementioned relative position shown in FIG. 2A between the X-ray source 2, the measuring object S, and the detection portion 42.

Further, as shown in FIG. 3B for example, the detection portion 42 may be arranged on the −X side from the measuring object S, while the X-ray source 2 may be movable from the −Z side to the +X side from the measuring object S. In the example shown in FIG. 3B, the relative position between the X-ray source 2, the measuring object S, and the detection portion 42 is also the same as the aforementioned relative position shown in FIG. 2A between the X-ray source 2, the measuring object S, and the detection portion 42.

Further, in the first embodiment, the X-ray device 1 may include a mechanism for adjusting the temperature of the internal space SP.

The control device 5 includes an information processing portion 100 (an information processing unit, an information processing member, or an information processing mechanism) and a storage portion 101 (a storage unit, a storage member, or a storage mechanism). The storage portion 101 stores the data detected by the detection apparatus 41 and the data detected by the detection portion 42. In the first embodiment, the data detected by the detection apparatus 41 are the data obtained when the measuring object S is irradiated with the X-ray XL from multiple directions, and the data representing the an absorption coefficient μ of the X-ray (to be referred to as "X-ray absorption data DX", below).

Here, the X-ray absorption coefficient μ is represented by the following formula.

$$\mu = -\ln(I/I_0)/x \qquad \text{[Formula 1]}$$

In the above formula, "$I_0$" represents the intensity of the X-ray XL irradiating the measuring object S from the X-ray source 2, "I" represents the intensity of the transmission X-ray transmitted through the measuring object S, "μ" represents the X-ray absorption coefficient of the measuring object S, and "x" represents the length of the passage path of the X-ray XL through the measuring object S.

In the first embodiment, a three-dimensional space is divided by a predetermined unit volume. By arranging the predetermined unit volume in the X direction, Y direction, and Z-axis direction, the three-dimensional space is expressed by the predetermined unit volume. In the first embodiment, the predetermined unit volume will be referred to below as a section. The predetermined unit volumes for a plurality of three-dimensional spaces may be referred to as voxels. The X-ray absorption coefficient μ is applied to each of the predetermined unit volumes. By applying the X-ray absorption coefficient μ to the predetermined unit volumes arranged three-dimensionally, it is possible to express the measuring object S of a three-dimensional shape by the absorption coefficient. By using a constant value for the predetermined unit volume or for the size of the predetermined volume in the three-dimensional space, the measuring object S may be expressed not only by, the absorption coefficient μ but also by $I/I_0$. In the first embodiment, an X-ray absorption data DX is used for reconstructing images by a back projection method in an aftermentioned information processing portion 100. Although the X-ray absorption data SX is supposed to be data representing the absorption coefficient μ in the first embodiment, without being limited to this example, it may be data of any form as long as usable in reconstructing images. Further, while the X-ray device 1 has the information processing portion 100 in the first embodiment, without being limited to this, the information processing portion 100 may be, for example, connected to a plurality of such X-ray devices 1.

In such a case, the information processing portion 100 is not provided in each of the plurality of X-ray devices 1, but the information from each of the plurality of X-ray devices 1 is sent to the information processing portion 100.

On the other hand, the data detected by the detection portion 42 are the data obtained by the detection portion 42 when the measuring object S is irradiated with the X-ray XL from one direction, and the data representing the intensity of the X-ray at each energy level of the X-ray (to be referred to as "X-ray spectrum data DS", below). The X-ray spectrum data DS detected by the detection portion 42 represents the intensity of the X-ray transmitted through the measuring object S at each wavelength of the X-ray. Further, by using the intensity of the X-ray irradiating the measuring object S, it is possible to represent, as a data at each wavelength of the X-ray, the ratio between the intensity of the X-ray irradiating the measuring object S at each wavelength, and the intensity of the transmission X-ray transmitted through the measuring object S.

The information processing portion 100 is configured to generate, from first detection information obtained by detecting the abovementioned transmission X-ray, second detection information different from the first detection information, according to the ratio between the first substance and the second substance contained in the measuring object S. Further, in the first embodiment, the information processing portion 100 generates the second detection information from first detection information, according to the abovementioned ratio between the first substance and the second substance. The detail of this process will be described later.

In the first embodiment, the ratio between the first substance and the second substance contained in the measuring object S is, for example, a volume ratio between the first substance and the second substance contained in the measuring object S. However, without being limited to this, it may be, for example, a weight ratio between the first substance and the second substance contained in the measuring object S. The first detection information and the second detection information are information related to the profile of a measuring object and the internal shape of the measuring object, and the second detection information is different from the first detection information. The first detection information is, for example, images related to the profile and internal shape of the measuring object S calculated from the X-ray absorption data DX. For example, the first detection information may be at least some of the images related to the profile and internal shape of the measuring object S calculated from the X-ray absorption data DX. For example, the first detection information may be images related to the profile and internal shape of the measuring object S at a certain position in the Y direction for the measuring object S placed on the table 12 shown in FIG. 1. Further, for example, the first detection information may be merely part of the internal shape of the measuring object S at a certain position in the V direction on the X-Y plane for the measuring object S placed on the table 12 shown in FIG. 1. That is, in the first embodiment, the first detection information is generated by applying the absorption coefficient to a plurality of sections on an image corresponding to a predetermined space including the measuring object S, and includes information for representing the profile of the measuring object S and the internal shape of the measuring object S. The second detection information is, for example, information related to the profile of the measuring object S and the internal shape of the measuring object S, and generated by image processing of the first detection information based on the ratio between the first substance and the second substance contained in the measuring object S. The second detection information may be either images representing the profile of the measuring object S and the internal shape of the measuring object S or numerical information used for representing those images.

FIG. 4 is a diagram showing an example of configuration of the information processing portion 100.

The information processing portion 100 includes a first information generation portion 110 (a first information generation unit, a first information generation member, or a first information generation mechanism), a ratio acquirement portion 120 (a ratio acquirement unit, a ratio acquirement member, or a ratio acquirement mechanism), and a second information generation portion 130 (a second information generation unit, a second information generation member, or a second information generation mechanism). The first information generation portion 110 is configured to represent the aforementioned first substance as a first absorption coefficient based on a result of detecting a plurality of transmission X-rays transmitted through the measuring object S irradiated with the X-ray in different directions, and to generate, as first detection information D1, information representing the aforementioned second substance as a second absorption coefficient different from the first absorption coefficient. In other words, the first information generation portion 110 is configured to generate a distribution of the X-ray absorption coefficient μ related to each substance as the first detection information D1, based on the X-ray absorption data DX which is the detection result of the detection apparatus 41. This distribution of the X-ray absorption coefficient μ corresponds to a tomographic image of the measuring object S represented as a distribution of the signal intensity according to the value of the absorption coefficient μ. In the first embodiment, the first information generation portion 110 uses the back projection method to generate, as the first detection information D1, the tomographic image represented by the distribution of the X-ray absorption coefficient μ from the X-ray absorption data DX. However, the present teaching is not limited to this example.

Further, "a plurality of transmission X-rays transmitted through the measuring object S irradiated with the X-ray in different directions" mentioned above mean a plurality of transmission X-rays corresponding respectively to the abovementioned plurality of directions, obtained when the measuring object S is irradiated with the X-ray from the plurality of different directions while rotating the measuring object S.

The ratio acquirement portion 120 is configured to calculate a ratio RT between the first substance and the second substance contained in the measuring object S, from the X-ray spectrum data DS which is a detection result of the detection portion 42. That is, the ratio acquirement portion 120 calculates the ratio RT between the first substance and the second substance based on information related to the first substance and the second substance obtained as the X-ray spectrum data DS (for example, information to identify, the type of a substance). The second information generation portion 130 is configured to generate the second detection information D2 from the first detection information D1 based on the ratio RT between the first substance and the second substance contained in the measuring object S. The type of each substance between the first substance and the second substance need not be identified with the X-ray spectrum data DS as long as, for example, the values of the absorption coefficient $\mu$ of the first substance and the second substance are calculated and obtained.

FIG. 5A is a diagram showing an example of the ratio acquirement portion 120.

In the first embodiment, the ratio acquirement portion 120 has a reference data RM of a transmission ratio of the X-ray radiated according to the X-ray energy through the first substance and the second substance. The ratio acquirement portion 120 calculates the ratio RT between the first substance and the second substance by comparing the detection result of the measuring object S with the detection portion 42, and the above reference data RM. In the first embodiment, it is possible to associate the reference data RM with the X-ray spectrum data DS based on the first substance and the second substance. Further, it is possible to use the reference data RM to calculate the ratio (proportion) RT between the first substance and the second substance included in the X-ray spectrum data DS. The ratio acquirement portion 120 is, as will be described later, configured to identify the ratio RT between the first substance and the second substance by comparing the spectrum of the X-ray spectrum data DS obtained from the detection portion 42, and the spectrum synthesized by addition of the spectrum of the first substance and the spectrum of the second substance included in the reference data DS. Of course, it is also possible to use another method different from the addition mentioned above to generate the spectrum synthesized from the spectrum of the first substance and the spectrum of the second substance.

In detail, the ratio acquirement portion 120 includes a reference data storage portion 121 (a reference data storage unit, a reference data storage member, or a reference data storage mechanism) and a ratio identification portion 122 (a ratio identification unit, a ratio identification member, or a ratio identification mechanism). The reference data storage portion 121 stores the reference data RM corresponding to the X-ray spectrum data DS. The ratio acquirement portion 122 is configured to identify the ratio RT between the first substance and the second substance from the reference data RM in conformity or near conformity with the information related to the first substance and the second substance, in the reference data RM stored in the reference data storage portion 121.

FIG. 5B shows an example of the reference data RM stored in the reference data storage portion 121. The reference data RM includes information related to the combination of a plurality of types of substances, information related to the ratio (volume ratio) between the plurality of types of substances, and a waveform data corresponding to the X-ray spectrum data DS extrapolated to be obtained form the transmission X-ray transmitted through the plurality of types of substances. The reference data RM includes, for example, a waveform data RM1 of the X-ray spectrum data DS obtained when the volume ratio is 4:1 between a substance A and a substance B with respect to the combination of the substance A and the substance B. In this case, from the waveform data RM1 of the X-ray spectrum data DS, it is possible to calculate that the volume ratio is 4:1 between the substance A and the substance B. The reference data RM includes the waveform data by combination of at an arbitrary ratio, a plurality of types of substances other than the substance A and the substance B. Further, the arbitrary ratio includes not only a combination of two types of substances but also combinations of three or more types of substances. Further, the reference data RM includes not only combinations of different substances but also waveform data of a single type. The reference data RM may be generated to create the waveform data RM1 based on the transmission X-ray transmitted through a substance in which the volume ratio is 4:1 between the substance A and the substance B. Further, the reference data RM need not have waveform data such as the waveform data RM1 but may only have corresponding values between the energy eV and the ratio ($I/I_0$) of X-ray intensity.

Figure 6:
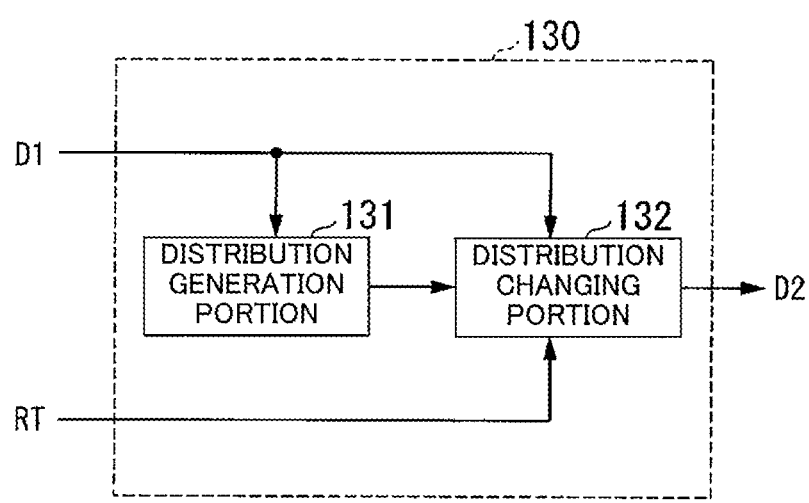
FIG. 6 is a diagram showing an example of a second information generation portion included in the information processing portion in accordance with the first embodiment.

FIG. 6 shows an example of the second information generation portion 130. In the first embodiment, the second information generation portion 130 includes a distribution generation portion 131 (a distribution generation unit, a distribution generation member, or a distribution generation mechanism) and a distribution changing portion 132 (a distribution changing unit, a distribution changing member, or a distribution changing mechanism). The distribution generation portion 131 is configured to generate, from the first detection information D1, a distribution of the value of signal intensity representing the absorption coefficient $\mu$ applied to the plurality of sections on the image corresponding to a predetermined space including the measuring object S. The distribution of the value of signal intensity is a statistical graph taking the number of sections on the vertical axis, and taking the value of signal intensity on the horizontal axis. By using this statistical graph, it is possible to calculate the frequency (proportion) of the absorption coefficient in the plurality of sections corresponding to the predetermined space. By virtue of this, it is possible to evaluate the distribution of the absorption coefficient $\mu$ applied to the plurality of sections in the predetermined space including the measuring object S. While examples of this distribution are shown in FIG. 12B, its details will be described later.

The distribution changing portion 132 can change the signal intensity indicating the absorption coefficient $\mu$ which forms the distribution of the absorption coefficient of the X-ray obtained as the first detection information D1. By virtue of this, it is possible to change the absorption coefficient applied to the plurality of sections on the image corresponding to the predetermined space including the measuring object S. The signal intensity indicating the absorption coefficient $\mu$ is changed based on the information related to the first substance and the second substance obtained as the aforementioned X-ray spectrum data DS, and the ratio RT between the first substance and the second substance. In the first embodiment, the absorption coefficient forming the distribution of the aforementioned X-ray absorption coefficient includes a first absorption coefficient corresponding to the first substance, and a second absorption coefficient corresponding to the second substance. Based on the above ratio RT, the distribution changing portion 132 changes the signal intensity indicating at least one of the first absorption coefficient and the second absorption coefficient.

Next, an explanation will be made for an example of operation of the X-ray device 1 in accordance with the first embodiment.

Figure 7:
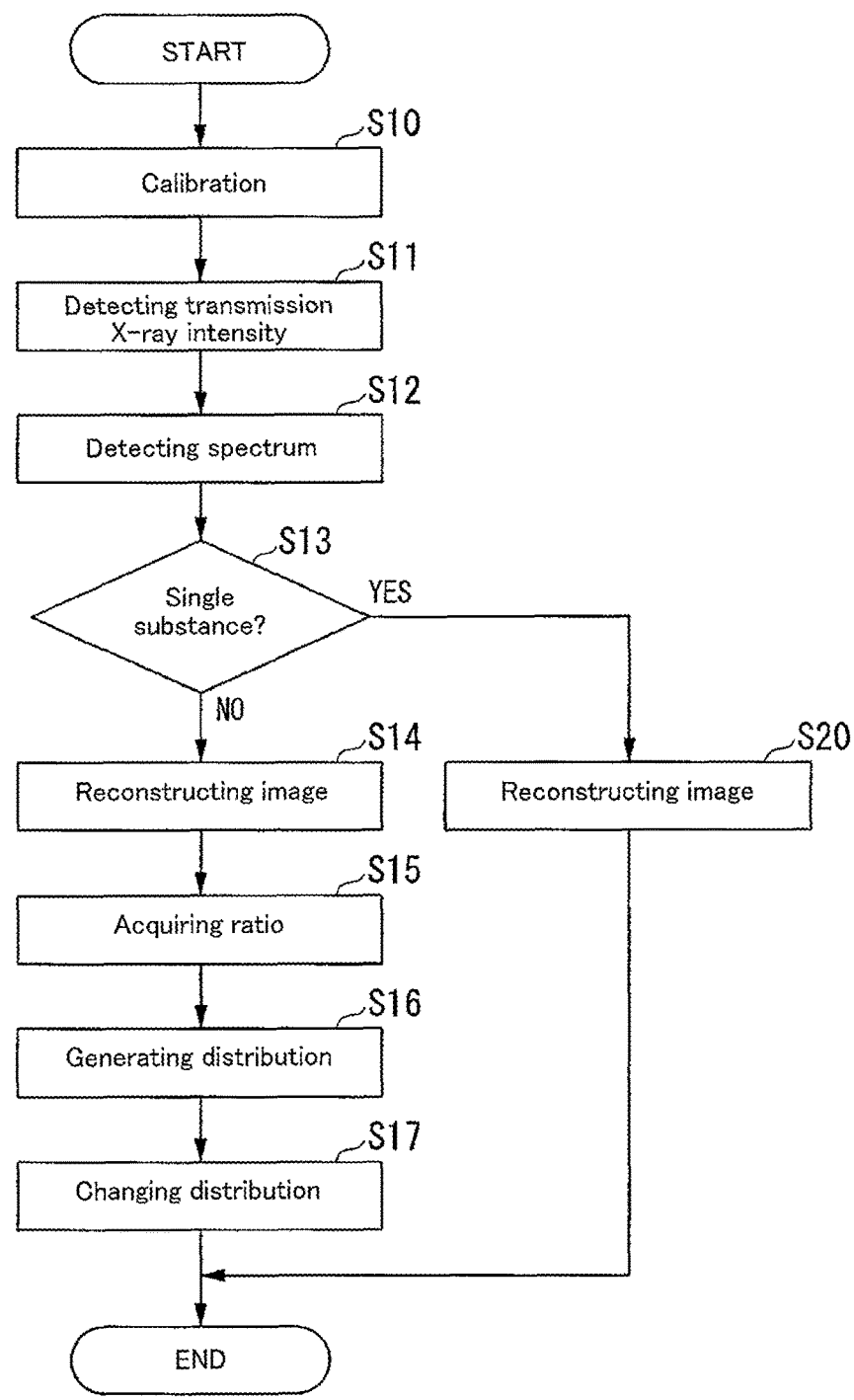
FIG. 7 is a flowchart showing a flow of operation of the X-ray device in accordance with the first embodiment.

FIG. 7 is a flowchart showing a flow of operation of the X-ray device 1 in accordance with the first embodiment. As shown in FIG. 7, the X-ray device 1 carries out: calibration (step S10), detecting the transmission X-ray with the detection apparatus 41 (step S11), detecting the spectrum of the transmission X-ray with the detection portion 42 (step S12), and the process of acquiring information related to the internal part of the measuring object S from each detection result of the detection apparatus 41 and the detection portion 42 (steps S13 to S17, and step 20).

First, the calibration (step S10) will be explained. In the first embodiment, an object of known size is irradiated with the X-ray. Then, a comparison is made between a dimension (ideal dimension) of the image obtained when the object of known size is arranged at a predetermined position, and a dimension (actual dimension) of the image obtained based on the transmission X-ray. Based on the result of the comparison, the step is then adapted to calculate a value for correcting the positional variation of the emission portion 8 of the X-ray source 2, and reflect the same in the measurement of the measuring object S. Further, the dimension of the image obtained based on the transmission X-ray is the dimension (size) of the image acquired by the detection apparatus 41, and includes, for example, the dimension of the image formed on the incidence surface 33.

If the temperature of the internal space SP changes, then it is possible that due to thermal deformation or the like, the relative position between the X-ray source 2, the measuring object S and the detection portion 4 changes and, as a result, the dimension of the image obtained based on the transmission X-ray varies. The calibration is carried out for obtaining a correction value to correct such variation of the dimension of the image. In the first embodiment, the calibration is not indispensable but may be omitted. In the calibration, the control device 5 causes the detection portion 42 to move in the +X direction as shown earlier in FIG. 2B. By virtue of this, it is possible for the detection apparatus 41 to detect the X-ray XL emitted from the X-ray source 2.

In the calibration, a reference member (illustration omitted) different from the measuring object S is retained on the table 12. In the first embodiment, the reference member is, for example, a spherical object. The profile (dimension) of the reference member is known. The reference member is an object restrained from thermal deformation. The reference member is an object which is restrained from thermal deformation at least to a greater extent than the measuring object S is restrained. Even if temperature changes in the internal space SP, the profile (dimension) of the reference member virtually does not change. Further, in the first embodiment, the reference member is not limited to a spherical shape.

The control device 5 measures the position of the stage 9 with the measuring system 28 while controlling the drive system 10 to adjust the position of the stage 9 retaining the reference member. The control device 5 adjusts the position of the stage 9 such that the reference member may be disposed in a reference position Pr.

The control device 5 causes the X-ray to be emitted from the X-ray source 2. The reference member is irradiated with the X-ray XL generated from the X-ray source 2. At a predetermined temperature Ta, if the reference member is irradiated with the X-ray XL from the X-ray source 2, then the X-ray XL irradiating the reference member is transmitted through the reference member. The transmission X-ray transmitted through the reference member is then incident on the incidence surface 33 of the detection apparatus 41. The detection apparatus 41 detects the transmission X-ray transmitted through the reference member. At the predetermined temperature Ta, the detection apparatus 41 detects an image of the reference member obtained based on the transmission X-ray transmitted through the reference member. In the first embodiment, the dimension (size) of the image of the reference member obtained at the predetermined temperature Ta is referred to as a dimension Wa.

Further, if the internal space SP is at a reference temperature Tr (ideal temperature or target temperature), then it is known in advance that a reference dimension Wr is fit to represent the dimension of the image acquired by the detection apparatus 41 based on the X-ray XL irradiating the reference member R disposed in the reference position Pr. Based on the relation between the dimension Wa obtained at the temperature Ta, and the reference dimension Wr at the reference temperature Tr, it is possible to correct the variation with temperature in the dimension of the image. In the first embodiment, the correction value is, for example, Wr/Wa for correcting the variation with temperature in the dimension of the image obtained based on the transmission X-ray.

In an aftermentioned process for acquiring the information related to the internal part of the measuring object S, for example, in the case of the dimension Ws of the image of the measuring object S obtained at the predetermined temperature Ta, the control device 5 multiplies the dimension Ws by the correction value Wr/Wa. That is, the control device 5 carries out the operation Ws×(Wr/Wa). By virtue of this, even when the actual temperature of the internal space SP is the predetermined temperature Ta, it is still possible to calculate the image (image dimension) of the measuring object at the reference temperature Tr.

Following the above calibration, the control device 5 carries out the detection of the transmission X-ray transmitted through the measuring object S (step S11). FIG. 8 is a schematic view for explaining an example of detecting the transmission X-ray. As shown in FIG. 8, in detecting the transmission X-ray, instead of the reference member mentioned above, the measuring object S is retained on the table 12. The control device 5 controls the stage device 3 to dispose the measuring object S between the X-ray source 2 and the detection apparatus 41.

The control device 5 measures the position of the stage 9 with the measuring system 28 while controlling the drive system 10 to adjust the position of the stage 9 retaining the measuring object S.

The control device 5 causes the X-ray to be emitted from the X-ray source 2. The measuring object S is irradiated with at least part of the X-ray XL generated from the X-ray source 2. If the measuring object S is irradiated with the X-ray XL from the X-ray source 2, then at least part of the X-ray XL irradiating the measuring object S is transmitted through the measuring object S. The transmission X-ray transmitted through the measuring object S is then incident on the incidence surface 33 of the detection apparatus 41. The detection apparatus 41 detects the transmission X-ray transmitted through the measuring object S. The detection result of the detection apparatus 41 is outputted to the control device 5. In the first embodiment, the detection result of the detection apparatus 41 is the X-ray absorption data DX mentioned before.

In the first embodiment, in order to change the area of irradiating the measuring object S with the X-ray XL from the X-ray source 2, the control device 5 causes the X-ray XL from the X-ray source 2 to irradiate the measuring object S while changing the position of the measuring object S. That is, the control device 5 causes the X-ray XL from the X-ray source 2 to irradiate the measuring object S at each of a plurality of positions of the measuring object S, and lets the detection apparatus 41 detect the transmission X-ray transmitted through the measuring object S.

In the first embodiment, the control device 5 changes the area of irradiating the measuring object S with the X-ray XL from the X-ray source 2 by rotating the table 12 retaining the measuring object S to change the position of the measuring object S relative to the X-ray source 2.

That is, in the first embodiment, the control device 5 causes the X-ray XL to irradiate the measuring object S while rotating the table 12 retaining the measuring object S. The detection apparatus 41 detects the transmission X-ray transmitted through the measuring object S at each position (each rotation angle) of the table 12.

Figure 9A:
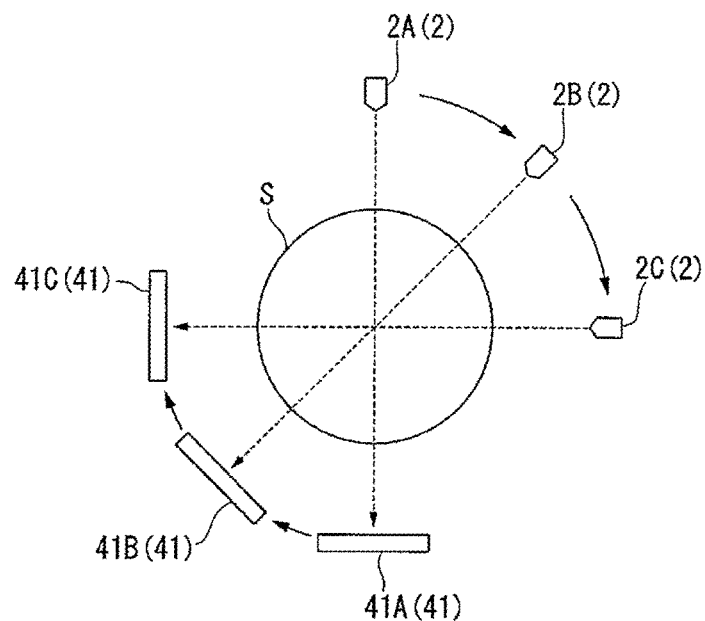
FIG. 9A is a view for explaining an example of an operation (detecting a transmission X-ray) of the X-ray device in accordance with the first embodiment.
Figure 9B:
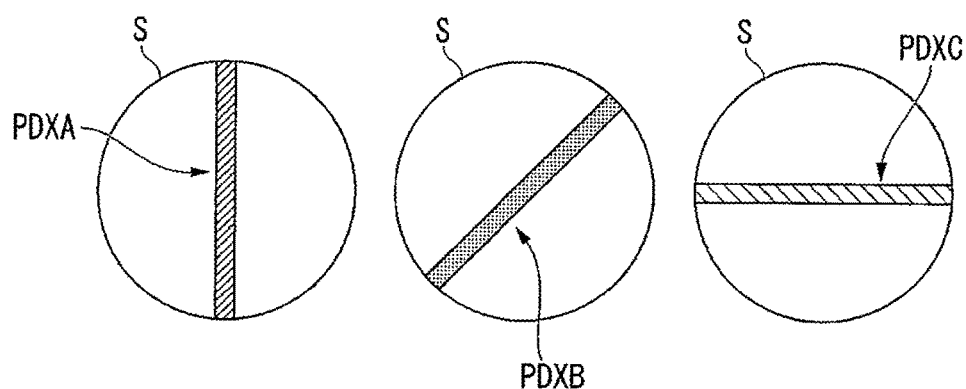
FIG. 9B is another view for explaining the example of the operation (detecting the transmission X-ray) of the X-ray device in accordance with the first embodiment.

FIGS. 9A and 9B are views for explaining the X-ray absorption data DX obtained from the transmission X-ray transmitted through the measuring object S on the rotating table 12. FIG. 9A is a view showing a relation of relative position between the measuring object S, the X-ray source 2, and the detection apparatus 41 when obtaining the X-ray absorption data DS. FIG. 9B is a view for explaining the meaning of the X-ray absorption data DX obtained by the detection apparatus 41 shown in FIG. 9A.

As described above, in detecting the transmission X-ray, the measuring object S on the table 12 is rotated. In other words, as shown in FIG. 9A, the X-ray source 2 and the detection apparatus 41 move around the measuring object S as relative to the measuring object S. In FIG. 9A, the X-ray sources 2A, 2B and 2C and the detection apparatuses 41A, 41B and 41C show how the X-ray source 2 and the detection apparatus 41 move relatively around the measuring object S in the clockwise direction with the measuring object S on the table 12 rotating in the counterclockwise direction.

As shown in FIG. 9A, with the measuring object S on the table 12 rotating, the measuring object S is irradiated with the X-ray from multiple directions, and the transmission X-ray from each direction of irradiation is detected by the detection apparatus 41. Then, the X-ray absorption data DX is obtained, corresponding to each direction of irradiation of the X-ray.

A pattern PDXA shown in FIG. 9B is obtained from the X-ray absorption data DX detected when the X-ray source 2 and the detection apparatus 41 are located in the positions of the X-ray source 2A and the detection apparatus 41A in FIG. 9A. This pattern PDXA represents the absorption coefficient μ on the passage path of the X-ray XL when the X-ray source 2 and the detection apparatus 41 are located in the positions of the X-ray source 2A and the detection apparatus 41A. Much the same is true on patterns PTB and PTC shown in FIG. 9B. Therefore, in the first embodiment, the X-ray absorption data DX represents the absorption coefficient μ on the passage path of the X-ray inside the measuring object S. For the convenience of explanation, while FIGS. 9A and 9B show an example of irradiating the measuring object S with the X-ray from three directions, the present teaching is not limited to this example.

The control device 5 lets the storage portion 101 store the X-ray absorption data DX obtained as a detection result of the detection apparatus 41. In the first embodiment, the X-ray absorption data DX is used as a data for generating the first detection information D1 which is the internal information of the measuring object S. For example, the X-ray absorption data DX is used as the data for using the back projection method to reconstruct a tomographic image of the measuring object S in the aftermentioned information processing portion 100.

Following the above detection of the transmission X-ray, the control device 5 carries out the detection of the spectrum of the transmission X-ray (step S12). In the first embodiment, as shown in FIG. 2A, the control device 5 causes the detection portion 42 to move in the −X direction. That is, the control device 5 causes the detection portion 42 to move to a predetermined position on the −Z side from the detection apparatus 41 on the passage path of the X-ray XL. By virtue of this, it is possible for the detection portion 42 to detect the spectrum of the transmission X-ray transmitted through the measuring object S.

In the first embodiment, when the detection portion 42 detects the spectrum of the transmission X-ray, the control device 5 stops the rotation of the table 12 retaining the measuring object S. That is, the control device 5 fixes the direction of the X-ray XL irradiating the measuring object S. However, without being limited to this example, the control device 5 may rotate the table 12 retaining the measuring object S. In this case, the measuring object S is irradiated with the X-ray from multiple directions, and it is possible to aggregate a plurality of spectra according to the irradiation directions of the X-ray respectively. By averaging the aggregated plurality of spectra, it is possible to stably detect the spectrum of the X-ray.

In the first embodiment, the control device 5 causes the X-ray XL to be generated from the X-ray source 2 with the table 12 stopped from rotation. The measuring object S is irradiated with at least part of the X-ray XL generated from the X-ray source 2. If the measuring object S is irradiated with the X-ray XL from the X-ray source 2, then at least part of the X-ray XL irradiating the measuring object S is transmitted through the measuring object S. The transmission X-ray transmitted through the measuring object S is then incident on an incidence surface 33S of the detection portion 42. The detection portion 42 detects the spectrum obtained by decomposing the transmission X-ray transmitted through the measuring object S at each energy level. The detection result of the detection portion 42 is outputted to the control device 5. The control device 5 lets the storage portion 101 store the detection result of the detection portion 42 as the X-ray spectrum data DS. An example of the X-ray spectrum data DS detected by the detection portion 42 is illustrated in, for example, FIG. 10C shown later.

Following the above detection of the X-ray spectrum, the control device 5 determines whether or not a single substance is contained in the measuring object S (step S13). In the first embodiment, the control device 5 determines whether or not a single type of substance is contained in the measuring object S from the X-ray spectrum data DS stored in the storage portion 101. Further, if it has been determined in advance whether or not a single type of substance is contained in the measuring object S, then this step may be omitted.

Figure 10A:
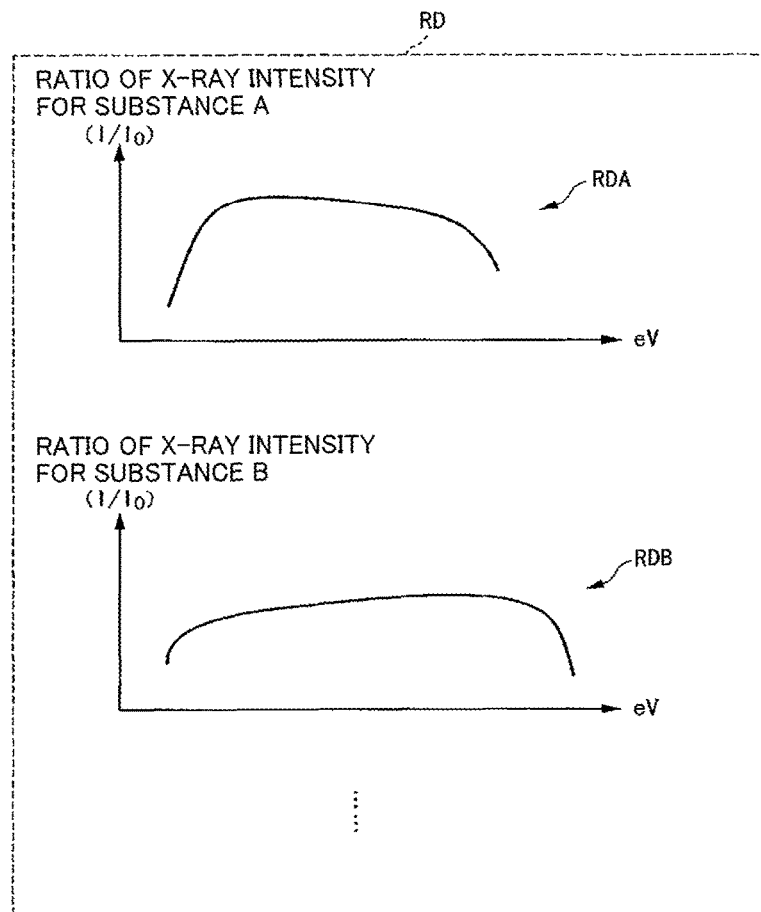
FIG. 10A is a diagram for explaining an example of an operation (determining the number of substances) of the device in accordance with the first embodiment.
Figure 10B:
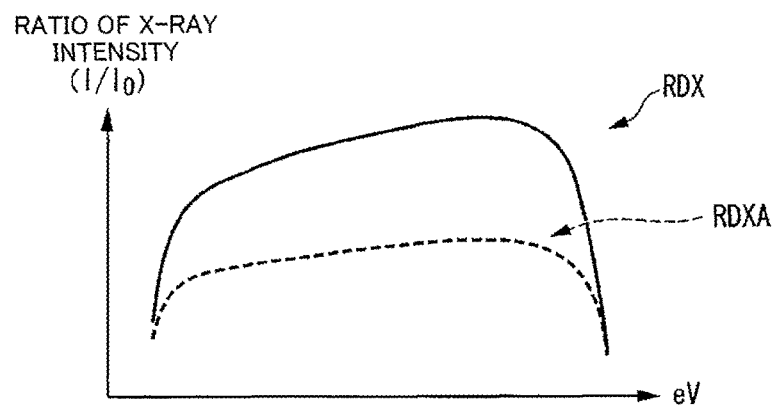
FIG. 10B is another diagram for explaining the example of the operation (determining the number of substances) of the X-ray device in accordance with the first embodiment.
Figure 10C:
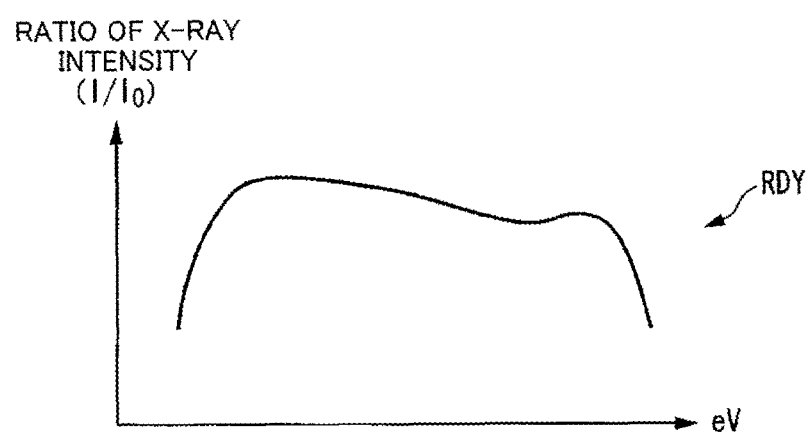
FIG. 10C is still another diagram for explaining the example of the operation (determining the number of substances) of the X-ray device in accordance with the first embodiment.

FIGS. 10A to 10C are explanatory diagrams for explaining the principle for determining whether or not a single type of substance is contained in the measuring object S, expressing the X-ray spectrum data DS by waveforms. In FIGS. 10A to 10C, the horizontal axis represents the X-ray energy (eV), while the vertical axis represents the ratio ($I/I_0$) between intensity $I_0$ of the X-ray irradiating the measuring object S per unit area of a plane orthogonal to the X-ray irradiation direction, and the intensity I of the transmission X-ray transmitted through the measuring object S.

FIG. 10A schematically shows, prepared in advance as a reference data RD, an X-ray spectrum data RDA of the substance A, and an X-ray spectrum data RDB of the substance B of a different type from the substance A. While FIG. 10A only shows the X-ray spectrum data RDA and RDB of the two types of substance A and substance B, the X-ray spectrum data of all possible substances contained in the measuring object S is prepared in advance as the reference data RD.

FIG. 10B schematically shows an X-ray spectrum data RDX (solid line) of the measuring object S detected by the detection portion 42. The value of the X-ray spectrum data RDX is influenced by the dimension and the like of the measuring object S, but the characteristic of its waveform is intrinsic to each substance. Therefore, by verifying whether or not the waveform characteristic of the X-ray spectrum data RDX shown in FIG. 10B conforms or nearly conforms with the waveform characteristic of the reference data RD shown in FIG. 9A, it is possible to determine whether or not a single type of substance is contained in the measuring object S. In this case, in order to eliminate the influence of the dimension and the like of the measuring object S, the height of the waveform of the X-ray spectrum data RDX is adjusted to such an extent as not to inhibit the waveform characteristic of the X-ray spectrum data RDX.

In the example shown in FIG. 10B, an X-ray spectrum data RDXA (wavy line) is obtained by adjusting the height of the X-ray spectrum data RDX. In the first embodiment, the height of the X-ray spectrum data RDX is adjusted by multiplying the X-ray spectrum data RDX by an appropriate weight in consideration of the influence of the dimension and the like of the measuring object S. The waveform characteristic of the X-ray spectrum data RDXA shown in FIG. 10B nearly conforms with the waveform characteristic of the X-ray spectrum data RDB forming the reference data RD shown in FIG. 10A. Therefore, it is possible to extrapolate that the same one type of substance as the substance B rendering the X-ray spectrum data RDB shown in FIG. 10A is contained in the measuring object S from which the X-ray spectrum data RDX shown in FIG. 10B is obtained.

In contrast to the above example, by multiplying an X-ray spectrum data RDY shown in FIG. 10C by an arbitrary weight, it is not possible to obtain any waveforms in conformity or near conformity with the absorption amount spectra RDA and RDB shown in FIG. 10A from this X-ray spectrum data RDY. Therefore, it is possible to extrapolate that at least not merely one type of the substance A and the substance B is contained in the measuring object from which the X-ray spectrum data RDY is obtained. Further, if nothing conforms or nearly conforms with any waveform of the reference data RD including the absorption amount spectra RDA and RDB shown in FIG. 10A even though the X-ray spectrum data RDY shown in FIG. 10C is multiplied by an arbitrary weight, then it is possible to extrapolate that not a single substance but a plurality of types of substances are contained in the measuring object S from which the X-ray spectrum data RDY shown in FIG. 10C is obtained. In the above manner, it is possible to determine whether or not a single type of substance is contained in the measuring object S. Further, if the types contained in the measuring object S are identified in advance, then it is possible to calculate each ratio of the identified types based on the X-ray spectrum data RDX of the measuring object S detected by the detection portion 42.

In the first embodiment, the control device 5 reads out, from the storage portion 101, the X-ray spectrum data DS obtained in the aforementioned step S12 and, according to the above principle, determines whether or not a single type of substance is contained in the measuring object S (step S13). If the control device 5 determines that a single type of substance is contained in the measuring object S (step S13: YES), then it uses an ordinary method, for example, to generate internal information of the measuring object S from the X-ray absorption data DX stored in the storage portion 101 (step S20). When a single type of substance is contained in the measuring object S, if the internal shape of the measuring object S is expressed by the absorption coefficient μ, then there is one type of value of the absorption coefficient μ. Therefore, because the X-ray absorption is constant in a predetermined space of the substance inside the measuring object S, false images are restrained from occurring with a change in radiation quality of the X-ray. By virtue of this, it is possible to express the profile of the measuring object S and the internal shape of the measuring object S by the absorption coefficient μ. In the first embodiment, the control device 5 uses the back projection method to reconstruct the tomographic image of the measuring object S from the X-ray absorption data DX.

On the other hand, if the control device 5 does not determine that a single type of substance is contained in the measuring object S (step S13: NO), that is, if it determines that a plurality of types of substances are contained in the measuring object S, then as will be explained below, the information processing portion 100 included in the control device 5 carries out a process (steps S14 to S17) for restraining quality deterioration of the information related to the internal part of the measuring object S The information processing portion 100 reads out the X-ray absorption data DX obtained in the aforementioned step S11 from the storage portion 101 of the control device 5. In the first embodiment, the first information generation portion 110 constituting the information processing portion 100 uses the back projection method to reconstruct the tomographic image of the measuring object S as the first detection information D1 from the aforementioned X-ray absorption data DX (step S14). In the first embodiment, from the X-ray absorption data DX, the first information generation portion 110 generates a distribution of the absorption coefficient μ for the inside of the measuring object S as the tomographic image. By virtue of this, an outline of the internal structure of the measuring object S is calculated. Hereinbelow, for the convenience of explanation, the term "spatial distribution" is used to refer to the distribution of the absorption coefficient μ corresponding to the tomographic image, and the distribution of the signal intensity on the image corresponding to this distribution of the absorption coefficient.

While the first information generation portion 110 generates the first detection information D1 by the back projection method in the first embodiment, the present intention is not limited to this example. As a method other than the back projection method for reconstructing a tomographic image of the measuring object S, for example, the filtered back projection method or the successive approximation method may be adopted. With respect to the back projection method and the filtered back projection method, descriptions are given in, for example, U.S. Patent Application Publication No. 2002/0154728. Further, with respect to the successive approximation method, a description is given in, for example, U.S. Patent Application Publication No. 2010/0220908.

Subsequently, the ratio acquirement portion 120 acquires the ratio RT between the plurality of types of substances (the first substance and the second substance) contained in the measuring object S, from the aforementioned X-ray spectrum data DS (step S15).

Figure 11:
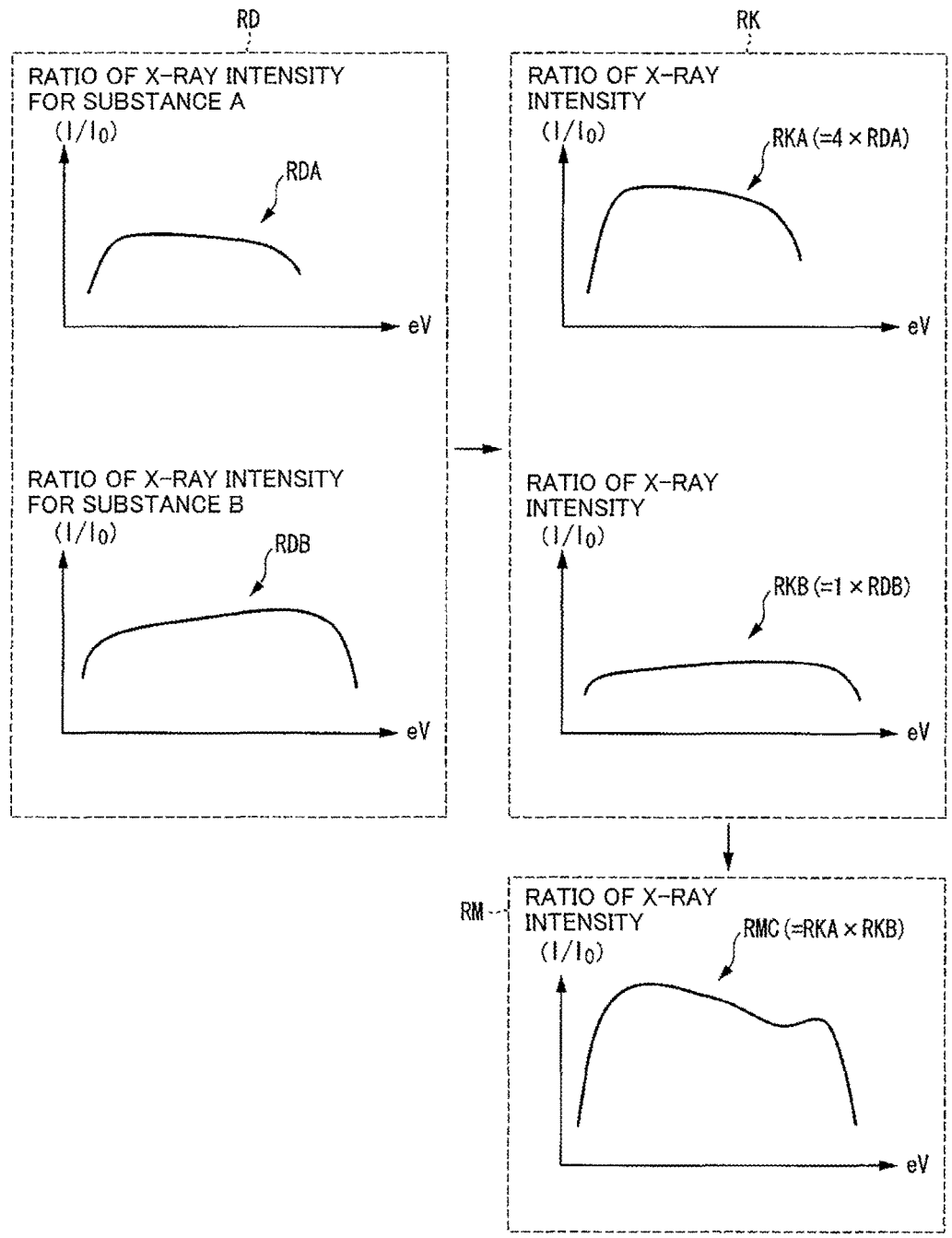
FIG. 11 is a diagram for explaining an example of an operation (acquiring ratios) of the ratio acquirement portion included in the information processing portion in accordance with the first embodiment.

FIG. 11 is an explanatory diagram for explaining the principle for acquiring the ratio RT between the plurality of types of substances contained in the measuring object S. Schematically in the first embodiment, the ratio RT between the plurality of types of substances contained in the measuring object S is identified by evaluating the degree of conformity or near conformity between the reference data RM thrilled from a combination of the X-ray spectrum data of a plurality of known types of substances, and the X-ray spectrum data DS obtained from the measuring object S. In the first embodiment, the reference data RM is, as will be described later, obtained by synthesizing every X-ray spectrum data of a plurality of known types of weighted substances. In the first embodiment, the ratio RT between the plurality of types of substances is, as also will be described later, identified by the weights for the X-ray spectrum data of the plurality of types of substances rendering the reference data RM in conformity or near conformity with the X-ray spectrum data DS obtained from the measuring object S.

The principle for acquiring the ratio RT between a plurality of types of substances will be explained below. The reference data RD shown in FIG. 11 includes the X-ray spectrum data RDA of the known substance A, and the X-ray spectrum data RDB of the known substance B. The X-ray spectrum data RDA of the known substance A is prepared in advance by letting the detection portion 42 detect the transmission X-ray transmitted through a measuring object which is made of only the substance A and whose dimension is prescribed (whose volume is prescribed). Likewise, the X-ray spectrum data RDB of the known substance B is prepared in advance by letting the detection portion 42 detect the transmission X-ray transmitted through a measuring object which is made of only the substance B and whose dimension is prescribed (whose volume is prescribed). The measuring object made of the substance A used for obtaining the X-rays spectrum data RDA, and the measuring object made of the substance B used for obtaining the X-ray spectrum data RDB have a profile of the same dimension.

In the example of FIG. 11, for the convenience of explanation, the reference data RD includes only the X-ray spectrum data RDA of the substance A and the X-ray spectrum data RDB of the substance B. However, the reference data RD may include an X-ray spectrum data of all types of substances which are possibly contained in the measuring object S to be measured by the X-ray device 1.

FIG. 11 shows a reference data RK which is obtained by multiplying the above reference data RD by an arbitrary weight. In the example shown in FIG. 11, an X-ray spectrum data RKA constituting the reference data RK is obtained by multiplying the X-ray spectrum data RDA constituting the reference data RD by the weight "4". This X-ray spectrum data RKA corresponds to the X-ray spectrum data obtained in the case of tripling the volume of the measuring object made of only the substance. A from which the X-ray spectrum data RDA is obtained to constitute the reference data RD. Further, an X-ray spectrum data RKB constituting the reference data RK is obtained by multiplying the X-ray spectrum data RDB constituting the reference data RD by the weight "1". This X-ray spectrum data RKB corresponds to the X-ray spectrum data obtained in the case of not changing the volume of the measuring object made of only the substance B from which the X-ray spectrum data RDB is obtained to constitute the reference data RD.

FIG. 11 shows an X-ray spectrum data RMC which constitutes the reference data RM, and is obtained by adding the X-ray spectrum data RKA, and the X-ray spectrum data RKB which constitute the above reference data RK. This means that the X-ray spectrum data RKC corresponds to the X-ray spectrum data of the measuring object containing the substance A and the substance B at such a volume ratio as to correspond to the ratio of the weight "4" to the weight "1" mentioned above. Therefore, if the X-ray spectrum data DS obtained from the transmission X-ray of the measuring object S conforms or nearly conforms with the X-ray spectrum data RKC constituting the reference data RM, then it is possible to extrapolate that the measuring object S contains the substance A and the substance B at the volume ratio of 4 to 1.

By changing the weights for the X-ray spectrum data RDA and RDB constituting the reference data RD, and preparing a plurality of X-ray spectrum data as the reference data RM in accordance with a combination of arbitrary weights, then it is possible to identify the arbitrary ratio RT (volume ratio) between the substance A and the substance B. Further, without being limited to a combination of the substance A and the substance B, by preparing a plurality of X-ray spectrum data as the reference data RM in accordance with a combination of a plurality of arbitrary types of substances, then it is possible to identify the ratio RT between the plurality of arbitrary types of substances. In the first embodiment, as shown in FIG. 5B mentioned before, the reference data storage portion 121 stores the waveform data (RM1 for example) of the X-ray spectrum data prepared in advance as the reference data RM, together with the above weight of each substance as the ratio (4:1 for example).

According to the above principle, the ratio identification portion 122 compares the X-ray spectrum data DS obtained from the measuring object S with the X-ray spectrum data stored as the reference data RM in the reference data storage portion 121. Then, the ratio identification portion 122 identifies the X-ray spectrum data in conformity or nearest conformity with the X-ray spectrum data DS acquired from the measuring object S (to be referred to as "nearly conformable X-ray spectrum data", below), in the spectrum data prepared as the reference data RM. Then, the ratio identification portion 122 acquires the ratio RT between the substances indicated by the nearly conformable X-ray spectrum data, from the reference data RM stored in the reference data storage portion 121. By virtue of this, the ratio identification portion 122 acquires the ratio RT between the plurality of types of substances contained in the measuring object S (step S15).

Subsequently, the distribution generation portion 131 constituting the second information generation portion 130 generates a frequency distribution representing the frequency of each signal intensity on the image, from the absorption coefficient distribution indicated by the first detection information D1 (step S16). In the first embodiment, this frequency distribution is, for example, a histogram whose horizontal axis (variable) represents the value which can be taken by each absorption coefficient in the absorption coefficient distribution obtained as the first detection information D1, and whose vertical axis represents the frequency of each signal intensity in the signal intensity distribution on the image corresponding to the absorption coefficient distribution indicated by the first detection information D1. In the first embodiment, the above frequency distribution is supposed to be a histogram but not limited thereto.

Figure 12A:
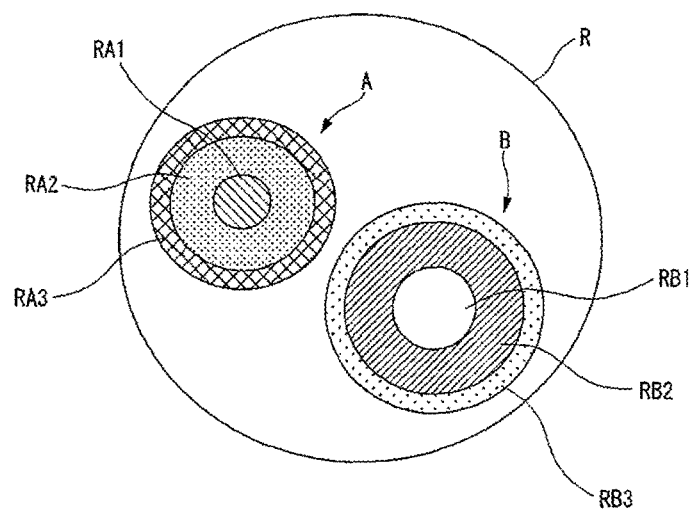
FIG. 12A is a view for explaining an example (frequency distributions before change) of an operation of the second information generation portion included in the information processing portion in accordance with the first embodiment.
Figure 12B:
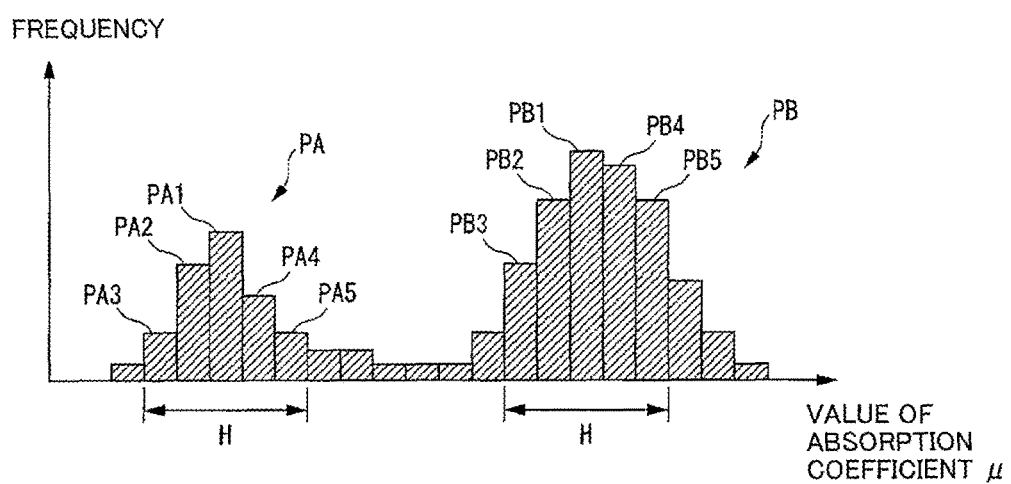
FIG. 12B is a graph for explaining an example (frequency distributions after change) of the operation of the second information generation portion included in the information processing portion in accordance with the first embodiment.

FIGS. 12A and 12B show an example of the method for the distribution generation portion 131 to generate the frequency distribution. FIG. 12A schematically shows an example of a spatial distribution of the signal intensity on the image corresponding to the distribution (tomographic image) of the absorption coefficient μ indicated by the first detection information D1. In the example shown in FIG. 12A, the substance A is represented by three areas RA1 to RA3 different in signal intensity, while the substance B is represented by three areas RB1 to RB3 different in signal intensity. FIG. 12B shows an example of the frequency distribution generated by the distribution generation portion 131 from the spatial distribution of the signal intensity shown in FIG. 12A. As shown in FIG. 12A, the area RA2 contacts with the area RA1 and the area RA3. That is, at each boundary, for example, at the boundary between the area RA1 and the area RA2, the divided section having the signal intensity applied to the area RA1 contacts with the divided section having the signal intensity applied to the area RA2. That is, the divided sections different in signal intensity contact with each other.

Further, the signal intensity allocated to the area RA2 is, in terms of degree, between the signal intensity corresponding to the area RA1 and the signal intensity corresponding to the area RA3. Therefore, along the extension portion of the substance A from its center, the signal intensity allocated to each divided section changes as the area turns to RA1, RA2, and RA3 via the boundaries.

The distribution generation portion 131 generates the frequency distribution shown in FIG. 12B by counting the frequency of the signal intensity belonging to each of the areas RA1, RA2, RA3, RB1, RB2, and RB3 shown in FIG. 12A. For example, suppose that the distribution generation portion 131 counts the frequency of the signal intensity belonging to the area RA1 of FIG. 12A, and let the count result be a frequency PA4 in the frequency distribution shown in FIG. 11B. Further, suppose that the distribution generation portion 131 counts the frequency of the signal intensity belonging to each of the areas RA2 and RA3 of FIG. 12A, and let the count results be frequencies PA1 and PA2 in the frequency distribution shown in FIG. 12B. Likewise, suppose that the distribution generation portion 131 counts the frequency of the signal intensity belonging to each of the areas RB1, RB2 and RB3 of FIG. 12A, and let the count results be frequencies PB4, PB1 and PB2 in the frequency distribution shown in FIG. 12B. Further, in order to simply the explanation, the number of the areas shown in FIG. 12A does not conform with the number of the frequencies in the frequency distribution shown in FIG. 12B.

The distribution changing portion 132 constituting the second information generation portion 130 generates the second detection information D2 from the first detection information D1 by changing the above frequency distribution of the signal intensity generated by the distribution generation portion 131, according to the information (absorption coefficient) related to the substances contained in the measuring object S obtained from the X-ray spectrum data DS, and the above ratio RT between the substances acquired by the ratio acquirement portion 120 (step S17).

Figure 13A:
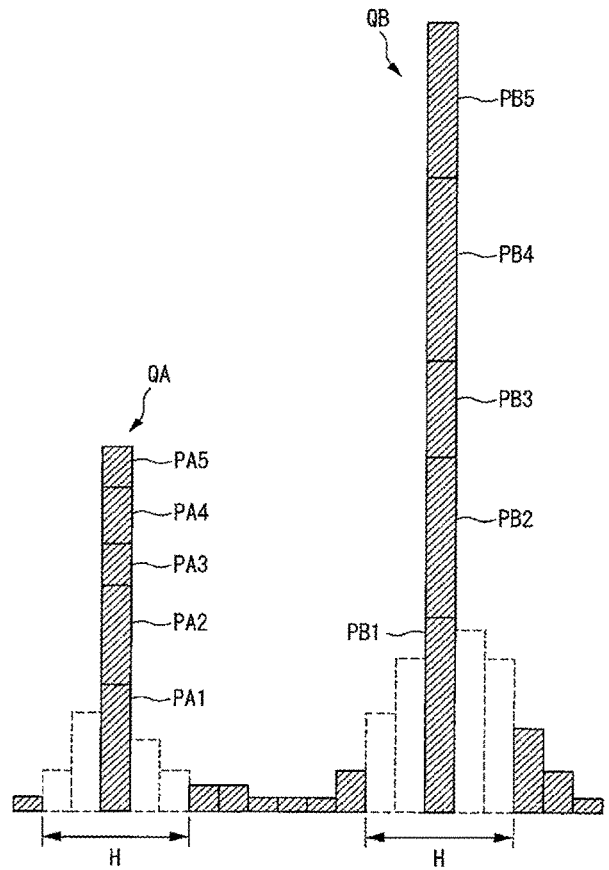
FIG. 13A is a graph for explaining an example (images corresponding to the frequency distributions before change) of the operation of the second information generation portion included in the information processing portion in accordance with the first embodiment.
Figure 13B:
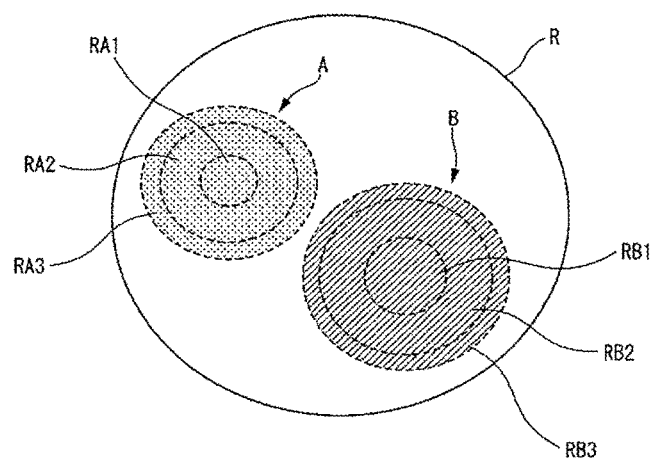
FIG. 13B is a view for explaining an example (images corresponding to the frequency distributions after change) of the operation of the second information generation portion included in the information processing portion in accordance with the first embodiment.

FIGS. 13A and 13B serve for explaining that the frequency distribution is changed by the distribution changing portion 132. FIG. 13A schematically shows an example of the frequency distribution of the signal intensity after the change, obtained by changing the frequency distribution of the signal intensity shown in FIG. 12B. For the distribution of FIG. 13, the vertical axis and the horizontal axis are the same as those of FIG. 12B. FIG. 13B schematically shows an example of the spatial distribution having the frequency distribution of the signal intensity shown in FIG. 13A. As will be explained below, the distribution changing portion 132 changes the frequency distribution having gentle peaks PA and PB shown in FIG. 12B as mentioned before into the frequency distribution having steep peaks QA and QB shown in FIG. 13A. Further, although three areas (actually) different in signal intensity are equalized in signal intensity in the first embodiment, two areas or four areas may be equalized. Further, it is desirable to equalize such areas as represented by signal intensities different from each other and as arranged to contact with each other. Therefore, in areas which are represented by signal intensities different from each other and which contact with each other at least partially, the second detection information D2 is created to equalize the signal intensities to each other. Further, when three areas different in signal intensity are equalized in signal intensity, the three signal intensities may be equalized to any one of the signal intensities, or may be changed into another signal intensity different from the three signal intensities.

For the convenience of explanation, a plurality of sections are defined to divide, into a grid-like pattern, a space of the image obtained from the first detection information D1 or the second detection information D2. Although for example one section in the first embodiment corresponds to one pixel on the image, it is not limited thereto. In the first embodiment, as shown in FIG. 13A, the distribution changing portion 132 changes at least one value of a first absorption coefficient and a second absorption coefficient obtained as the first detection information corresponding respectively to the substance A and the substance B, so as to lessen the types of value of the absorption coefficient applied to the plurality of sections on the image obtained as the second detection information D2. In the first embodiment, the distribution changing portion 132 lessens the types of value of the absorption coefficient applied to the plurality of sections on the image obtained as the second detection information D2, to let the same be less than the types of value of the absorption coefficient applied to the plurality of sections on the image obtained as the first detection information D1.

Here, the types of value of the absorption coefficient represent the difference of value of the absorption coefficient on the horizontal axis with the frequency present in the frequency distribution shown in FIG. 12B or in FIG. 13A. In FIG. 12B for example, there are two types of value of the absorption coefficient represented by the frequencies PA2 and PA3 on the horizontal axis, corresponding to those frequencies PA2 and PA3, while there are totally 20 types of value of the absorption counting, corresponding to the number of frequencies. On the other hand, in the frequency distribution shown in FIG. 13A, there are lessened to 12 types of value of the absorption coefficient on the horizontal axis. In this manner, the distribution changing portion 132 changes the frequency distribution shown in FIG. 12B to lessen the types of value of the absorption coefficient applied to the plurality of sections on the image in the frequency distribution after the change shown in FIG. 13A. As will be described later, in the process of changing the frequency distribution, the distribution changing portion 132 integrates a plurality of frequencies in the frequency distribution into a smaller number of frequencies than the number of the former plurality of frequencies.

Further, in the first embodiment, based on the information (absorption coefficient) related to the first substance and the second substance obtained as the X-ray spectrum data DS from the transmission X-ray, and the ratio between the first substance and the second substance, the distribution changing portion 132 changes, into a third absorption coefficient, at least one of the first absorption coefficient and the second absorption coefficient corresponding to the substance A and the substance B obtained from the first detection information D1. In other words, based on the ratio RT between the first substance and the second substance obtained from the above X-ray spectrum data DS, the distribution changing portion 132 changes at least one of the first absorption coefficient and the second absorption coefficient corresponding respectively to the substance A and the substance B obtained from the first detection information D1.

Next, referring to FIGS. 14A to 14C, an explanation will be made on a method for changing the aforementioned frequency distribution shown in FIG. 12B into the frequency distribution shown in FIG. 13A.

In the first embodiment, based on the information (i.e., the absorption coefficient) related to the types of substances contained in the measuring object S obtained from the X-ray spectrum data DS, the center of the frequency distribution after change (a position in the frequency distribution on the horizontal axis) is identified. Further, the scope of the frequency distribution is identified with the above center as the starting point according to the ratio RT of the substances contained in the measuring object S. Further, the frequency distribution is changed by integrating the frequency included in the above scope in the distribution before change into the frequency positioned at the center.

In the first embodiment, the information for identifying the center of the frequency distribution after change, and the intonation related to the ratio RT are obtainable from the reference data RM shown in FIG. 5B referenced by the aforementioned ratio acquirement portion 120 in the process of acquiring the ratio RT. That is, according to the reference data RM shown in FIG. 5B, the types of the substance A and the substance B rendering the ratio RT are identified. If the type of each substance is identified, then the absorption coefficient of that substance is identified. Therefore, the absorption coefficient of each substance contained in the measuring object S is identified by acquiring the ratio RT between the substance A and the substance B and, from this absorption coefficient, the center of each distribution is identified to correspond to the substance A and the substance B in the frequency distribution after change shown in FIG. 13A.

Figure 14A:
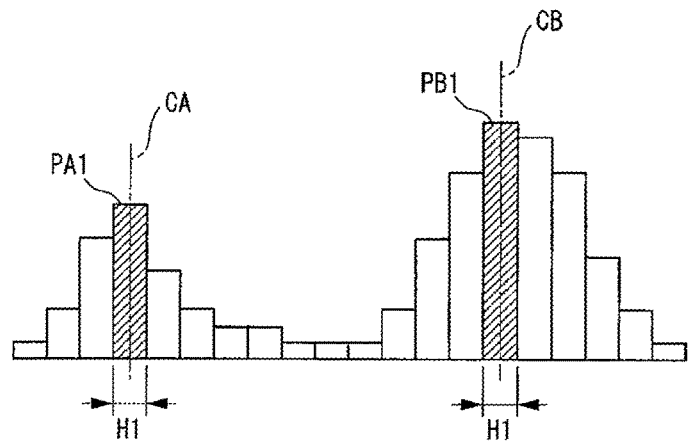
FIG. 14A is a graph for explaining an example (a method of changing the frequency distributions) of the operation of the second information generation portion included in the information processing portion in accordance with the first embodiment.

As shown in FIG. 14A, the distribution changing portion 132 identifies centers CA and CB of the distributions corresponding to the respective substances in the frequency distribution after change, based on the information (i.e., the absorption coefficient) related to the types of the substances obtained from the X-ray spectrum data DS. That is, as described above, the distribution changing portion 132 sets the values of the absorption coefficient corresponding to the types of the respective substances identified when the ratio acquirement portion 120 acquires the ratio RT, as the centers CA and CB of the frequency distributions.

Subsequently, according to the ratio RT of the substances contained in the measuring object S acquired by the ratio acquirement portion 123, the distribution changing portion 132 identifies scopes of the distributions before change with the centers CA and CB as the starting points. In detail, as shown in FIG. 14A, the distribution changing portion 132 at first sets scopes H1 including only the frequencies positioned at the centers CA and CB, and calculates the ratio of the frequencies corresponding to the respective substances belonging to the scopes. In this example, the ratio is calculated between one frequency (hatched) included in the scope set for the center CA, and one frequency (hatched) included in the scope H1 set for the center CB. Then, the distribution changing portion 132 deter nines whether or not this frequency ratio conforms or nearly conforms with the ratio RT acquired by the ratio acquirement portion 120.

Figure 14B:
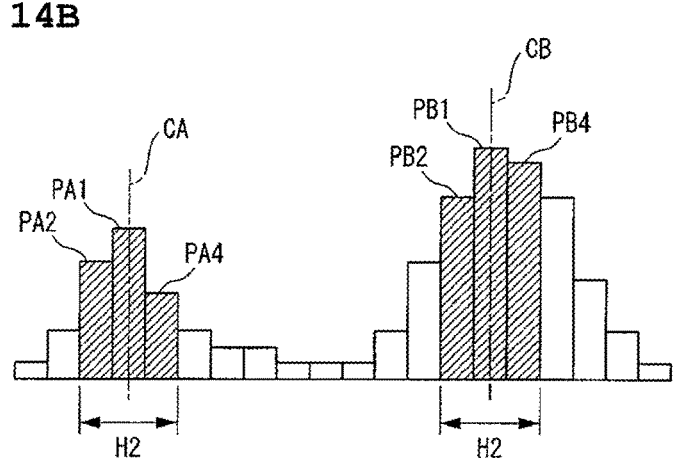
FIG. 14B is another graph for explaining the example (the method of changing the frequency distributions) of the operation of the second information generation portion included in the information processing portion in accordance with the first embodiment.
Figure 14C:
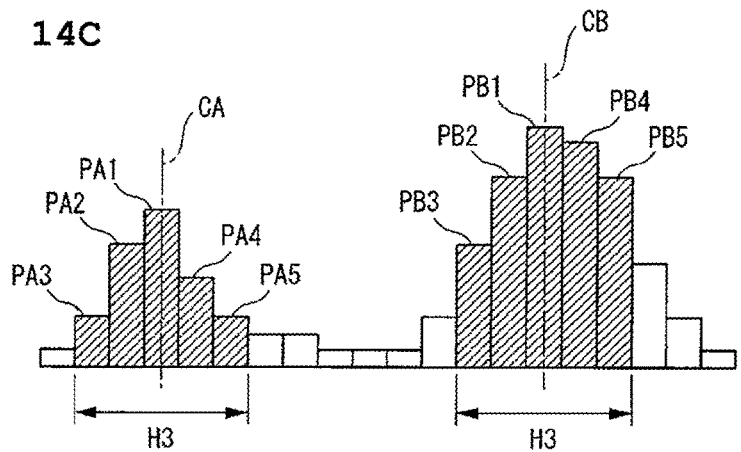
FIG. 14C is still another graph for explaining the example (the method of changing the frequency distributions) of the operation of the second information generation portion included in the information processing portion in accordance with the first embodiment.

If the above frequency ratio does not conform or nearly conform with the ratio RT, then, as shown in FIG. 14B, the distribution changing portion 132 increases the scopes H1 by a certain value to expand the same to scopes H2, and calculates the ratio of the frequencies belonging to the scopes H2. In this example, the ratio is calculated between three frequencies (hatched) included in the scope H2 set for the center CA, and three frequencies (hatched) included in the scope H2 set for the center CB. Then, the distribution changing portion 132 determines whether or not this frequency ratio conforms or nearly conforms with the ratio RT.

In this manner, the distribution changing portion 132 gradually expands the scopes with the centers CA and CB as the starting point until the frequency ratio conforms or nearly conforms with the ratio RT. Then, as shown in FIG. 14C, when the scopes H2 are expanded to scopes H3, if the ratio of the frequencies belonging to the scopes H3 conforms or nearly conforms with the ratio RT, then the scopes H3 are identified as the scopes according to the ratio RT of the substances contained in the measuring object S.

Subsequently, the distribution changing portion 132 integrates the plurality of frequencies belonging to the scopes H3 identified above into a smaller number of frequencies than the number of the plurality of frequencies. In the first embodiment, the frequencies PA2, PA3, PA4 and PA5 included in the one scope H3 in the frequency distribution before change are integrated into the frequency PA1 positioned at the center CA of the distribution after change. Likewise, the frequencies PB2, PB3, PB4 and PB5 included in the other scope H3 in the frequency distribution before change are integrated into the frequency PB1 positioned at the center CB of the distribution after change. As a result, as shown in FIG. 13A mentioned before, the frequency distribution having the steep peaks QA and QB is obtained. In other words, the distribution changing portion 132 changes the frequency distribution having the peaks PA and PB of a comparatively large half value width as shown in FIG. 12B mentioned before, into the frequency distribution having the peaks QA and QB of a smaller half-value width than the peaks PA and PB shown in FIG. 13A. Further, as shown in FIG. 12B, the PA1 of the highest frequency is there in the peak PA within a predetermined range of the value of the absorption coefficient μ. There are also the PA2 and PA4 of lower frequencies than the PA1. Hence, in FIG. 12B, the frequency distributions have peaks. Further, in FIG. 13A, although the frequency distributions are changed to have smaller half value width, for example, it is also possible to narrow the width, with respect to the mode value, at 30% of the number of the divided sections in terms of the magnitude of the value of the absorption coefficient μ and, as a result, the value at 50% of the number of the divided sections may decrease with respect to the mode value. Of course, the number of the divided sections may also be 90%, 80%, 70%, 60%, 40%, 30%, 20%, and 10% with respect to the mode value. Of course, it may also be other percentages than the above. Further, as shown in FIG. 12B, there is a mode value for each of the two scopes H. Further, as shown in FIG. 12B, for each of the two scopes H, the magnitude of the mode value is different. Further, the mode values for a plurality of scopes H may have the same magnitude. Further, while there are two mode values and there is a scope H for each mode value in FIG. 12B, the number of mode values is not limited to two. For example, the number of mode values may also be three, four, five, or more.

Here, in the first embodiment, the distribution changing portion 132 generates the second detection information D2 by correcting the first detection information D1 such that the frequency distributions shown in FIG. 13A may be obtained. That is, the distribution changing portion 132 changes the signal intensity of the pixels corresponding to each frequency integrated into the frequencies of the centers CA and CB in the process of generating the frequency distributions of FIG. 13A, into the signal intensity of the pixels corresponding to the frequencies of the centers CA and GB. In other words, the distribution changing portion 132 changes the frequency distributions to make different values become one value in a predetermined scope of a frequency distribution. That is, it changes the frequency distribution such that the value of one of adjacent divided sections may become equal to the value of the other. By virtue of this, the second detection information D2 is generated from the first detection information D1.

Corresponding to the frequency distributions having the steep peaks QA and QB shown in FIG. 13A, there is a clear image G4 obtained from the second detection information D2. The two types of the substance A and the substance B have uniformized respective gradations, thereby enabling an easy identification of each substance.

As explained above, according to the first embodiment, because the first detection information D1 is changed to the second detection information D2 which indicates an image having steep frequency distributions, from this second detection information D2, it is possible to clearly identify the internal substances of the measuring object S. Therefore, even if the measuring object S contains a plurality of types of substances, it is still possible to restrain any defective measurement associated with the influence of any false image. Further, according to the first embodiment, because it is possible to clearly identify the internal substances of the measuring object S, it is possible to use the X-ray device 1 according to the first embodiment in measuring the internal shape of the measuring object S.

Further, while the detection portion 42 identifies the types of the plurality of substances contained in the measuring object S in the first embodiment, the identifying method is not limited to this. For example, two types of X-ray of different radiation quality may irradiate the measuring object S from the X-ray source 2. The radiation quality may be varied by varying the transmissivity of the X-ray through a filter arranged between the X-ray source 2 and the measuring object S. By virtue of this, the X-ray radiated from the X-ray source 2 is separated by the filter to take on different wavelengths. In this case, by comparing the intensities of the transmission X-ray from the two types of X-ray different in radiation quality, it is possible to identify the types of the plurality of substances contained in the measuring object S without using the transmission intensity of the X-ray at each wavelength. That is, the wavelength of the X-ray produced from the X-ray source 2 need not be changed continuously. Of course, for example, the wavelength of the X-ray produced from the X-ray source 2 may be changed continuously. For example, the measuring object S is irradiated with the X-ray of a wavelength in a predetermined range from the X-ray source 2. The wavelength in the predetermined range may be varied in turn to identify the types of the plurality of substances contained in the measuring object S.

Further, while the detection portion 42 and the detection apparatus 41 are different members in the first embodiment, they may be constructed of an identical member. For example, the X-ray spectrum data DS may be generated in the detection apparatus 41. For example, in the scintillator portions 34 of the detection apparatus 41, suppose that conversion into a light ray, of a different wavelength is possible according to the wavelength of the incident X-ray. By calculating the spectrum of the light ray converted from the X-ray, the wavelength of the incident X-ray is extrapolated, and the X-ray spectrum data DS is generated.

Further, when the detection portion 42 detects only part of the transmission X-ray through the measuring object S, for example, along the Y-axis direction of FIG. 1, the position of irradiating the measuring object S may be changed to let the detection portion 42 detect the X-ray transmitted through the measuring object S a plurality of times, in this case, the types of the plurality of substances contained in the measuring object S may be identified from the result by the detection portion 42 as the result of the X-ray transmitted through the measuring object S, based on the X-ray transmitted through the measuring object S at each of the plurality of times.

Further, while the X-ray spectrum data RDX and X-ray absorption data DX for the measuring object S are calculated in the same devise in the first embodiment, they may be obtained respectively in different devices.

Second Embodiment

Next, a second embodiment will be explained.

Figure 15:
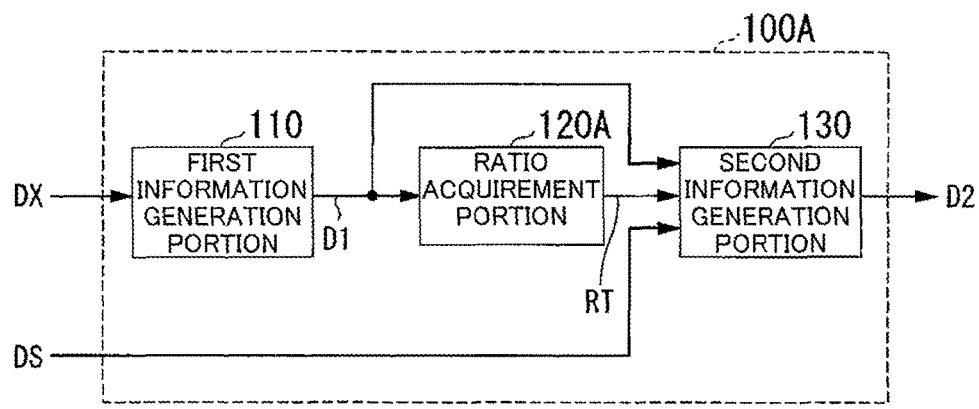
FIG. 15 is a diagram showing an example of an information processing portion included in the X-ray device in accordance with a second embodiment.

FIG. 15 shows an example of an information processing device 100A according to the second embodiment. An X-ray device according to the second embodiment includes the information processing portion 100A shown in FIG. 15 instead of the information processing portion 100 in the configuration of the X-ray device 1 according to the first embodiment described above. The information processing portion 100A includes a ratio acquirement portion 120A, instead of the ratio acquirement portion 120 provided in the information processing device 100 according to the first embodiment described above, to acquire the ratio of substances from the first detection information D1. In the second embodiment, the ratio acquirement portion 120A acquires the ratio of the substances contained in the measuring object S from the signal intensity distribution indicated by the first detection information D1. The other configurations are the same as in the first embodiment described above.

Figure 16:
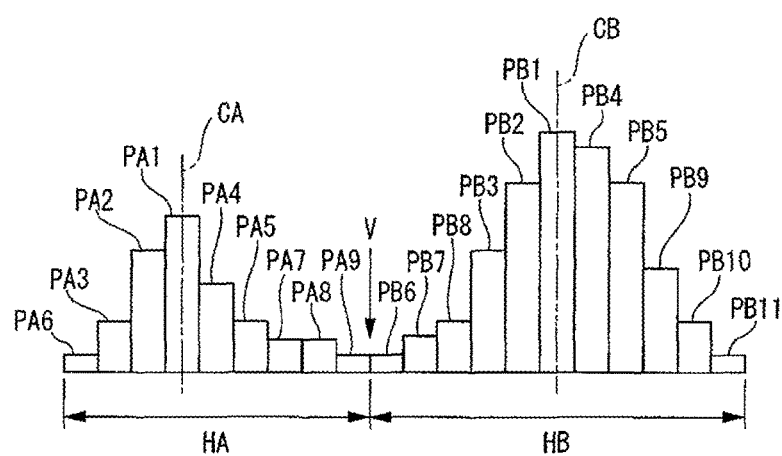
FIG. 16 is a graph for explaining an example of an operation (acquiring ratios) of the information processing portion in accordance with the second embodiment.

Referring to FIG. 16, an explanation will be made on a method for the ratio acquirement portion 120A to acquire the ratio. FIG. 16 shows frequency distributions corresponding to FIG. 12B according to the aforementioned first embodiment. The ratio acquirement portion 120A identifies the position of the trough of the frequency distributions shown in FIG. 16, as a boundary value V of the frequency belonging to each of the two substance A and substance B. Then, the ratio acquirement portion 120A calculates the ratio between the frequencies belonging to a scope HA and a scope HB divided by the boundary value V, and uses the ratio as the ratio RT of the substances contained in the measuring object S. In the example of FIG. 16, the frequencies PA1 to PA9 belong to the scope HA, while the frequencies PB1 to PB11 belong to the scope HB. In the second embodiment, the ratio acquirement portion 120A acquires the ratio between the summation of the frequencies PA1 to PA9 and the summation of the frequencies PB1 to PB11, as the ratio RT between the substance A and the substance B.

The frequency distributions shown in FIG. 16 are the same as the frequency distributions shown in FIG. 12B in the aforementioned first embodiment. Therefore, in order to generate the histogram shown in FIG. 16, the ratio acquirement portion 120A according to the second embodiment may use the function for the second information generation portion 130 according to the first embodiment to generate the frequency distributions shown in FIG. 12B. Conversely, in order to generate the frequency distributions shown in FIG. 12B, the second information generation portion 130 according to the first embodiment may use the function for the ratio acquirement portion 120A according to the second embodiment to generate the frequency distributions shown in FIG. 16. The other aspects are the same as in the aforementioned first embodiment.

According to the second embodiment, it is possible to acquire the ratio RT of a plurality of types of substances in a comparatively simpler manner than in the first embodiment. Hence, it is possible to reduce the processing burden for generating the second detection information from the first detection information.

Third Embodiment

Next, a third embodiment will be explained,

In the third embodiment, the second detection information D2 obtained in the aforementioned first embodiment and second embodiment is corrected to form an image reflecting the internal state of the measuring object S.

Figure 17:
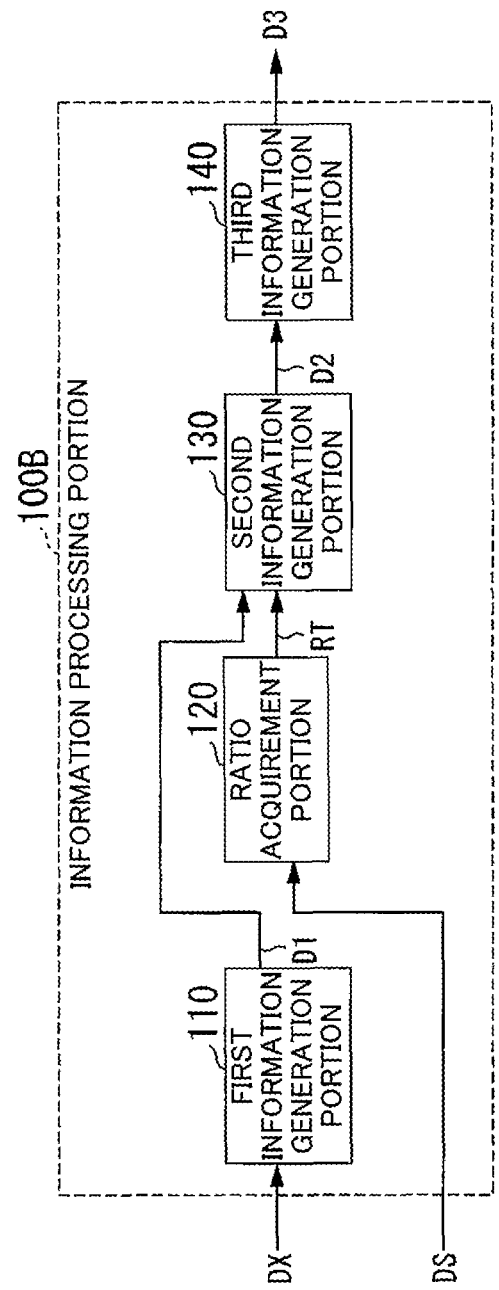
FIG. 17 is a diagram showing an example of an information processing portion included in the X-ray device in accordance with a third embodiment.

FIG. 17 shows an example of an information processing device 100B according to the third embodiment. An X-ray device according to the third embodiment includes the information processing portion 100B shown in FIG. 17 instead of the information processing portion 100 in the configuration of the X-ray device 1 according to the aforementioned first embodiment. The information processing portion 100B further includes a third information generation portion 140 (a third information generation unit, a third information generation member, or a third information generation mechanism) in the configuration of the information processing device 100 according to the aforementioned first embodiment. The other configurations are the same as in the aforementioned first embodiment. Further, it is possible to apply the configuration of the third embodiment to the second embodiment.

Figure 18:
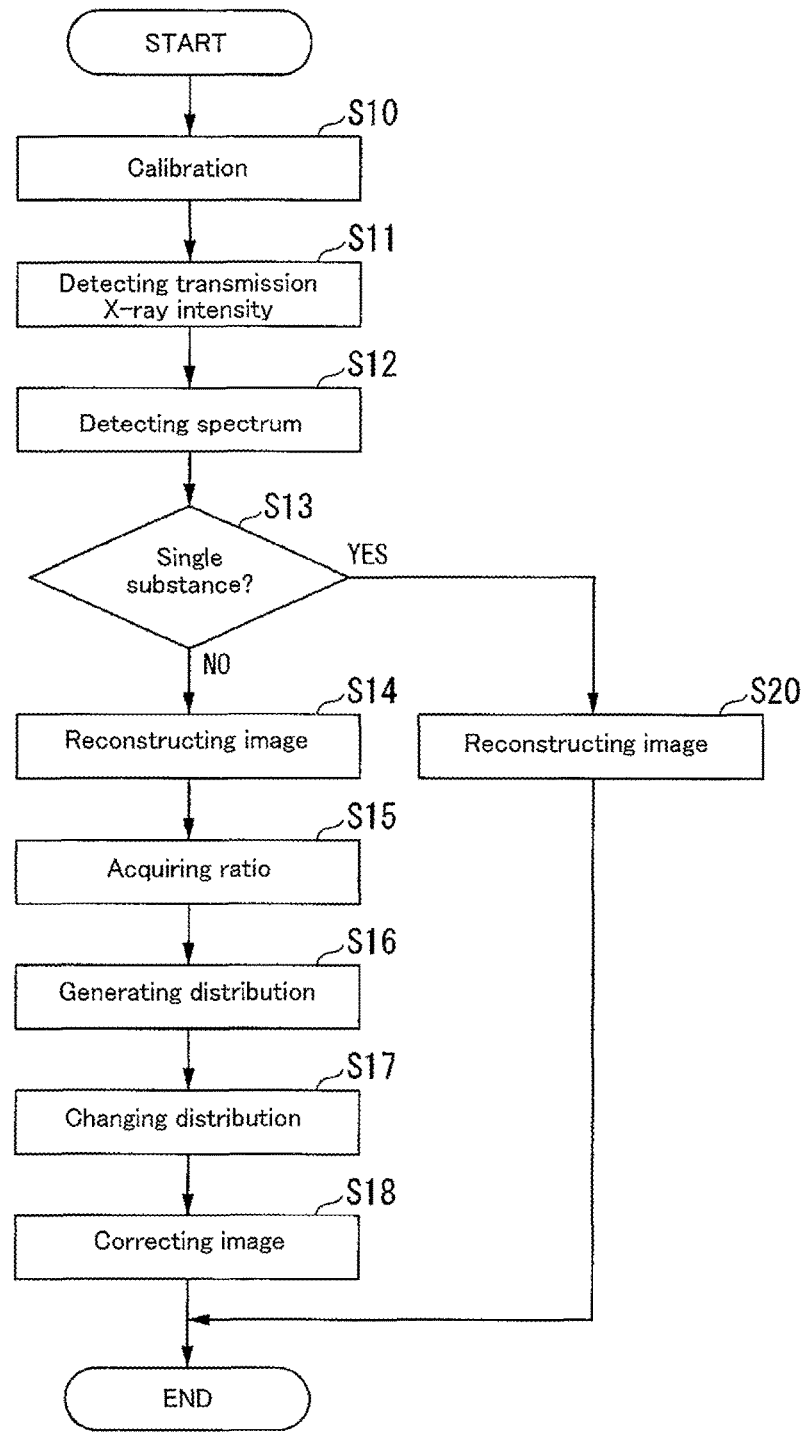
FIG. 18 is a flowchart showing a flow of operation of the X-ray device in accordance with the third embodiment.

FIG. 18 is a flowchart showing a flow of operation of the X-ray device including the information processing portion 100B according to the third embodiment. In FIG. 18, the steps S10 to S17 and the step S20 are the same as those of the operation of the X-ray device 1 according to the first embodiment shown in FIG. 7 mentioned before. In the third embodiment, a step S18 is added to be carried out by the third information generation portion 140.

The third information generation portion 140 according to the third embodiment generates third detection information D3 with the second detection information as the initial value such that a computation result according to the successive approximation method may conform with the actual detection result. By virtue of this, the actual internal state of the measuring object S is reflected in the third detection information. Therefore, it is possible to have a more detailed knowledge of the internal state of the measuring object S than in the first embodiment.

Fourth Embodiment

Next, with reference to FIGS. 17 and 18 of the third embodiment described above, a fourth embodiment will be explained. In the fourth embodiment, the third information generation portion 140 shown in FIG. 17 uses the back projection method instead of the successive approximation method to generate the third detection information D3 from the second detection information D2. The other configurations are the same as in the third embodiment.

The third information generation portion 140 according to the fourth embodiment identifies the arrangement of the substances contained in the measuring object S, based on the ratio RT of the plurality of types of substances acquired by the ratio acquirement portion 120. Then, the third information generation portion 140 causes the second detection information D2 to reflect the information related to the identified arrangement of the substances. Then, the third information generation portion 140 applies the back projection method to the second detection information D2 reflecting the arrangement of the substances to generate the third detection information D1 in the fourth embodiment, to cause the second detection information D2 to reflect the arrangement of the substances means to cause the second detection information D2 to reflect the absorption coefficient of the substances contained in the measuring object S obtained from the X-ray spectrum data DS.

FIG. 19 is an explanatory view for explaining the method for causing the second detection information D2 to reflect the arrangement of the substances. FIG. 19 shows a pattern J1 which is a pattern obtained by forward projection of the second detection information D2, as well as a pattern before the arrangement of the substances is reflected in the second detection information D2. The pattern J1 corresponds to the pattern PDXC shown in FIG. 9B which is a pattern before the back projection by the first information generation portion 110, in that the pattern J1 is a pattern before the back projection by the third information generation portion 140.

FIG. 19 shows a pattern J2 which is a pattern in which the arrangement of the substances is reflected in the above pattern J1. In the pattern J2, the absorption coefficient according to the arrangement of the substances is reflected in a partial area F. The third information generation portion 140 generates the second detection information D2 reflecting the substance arrangement by the back projection using the pattern J2.

In the fourth embodiment, the third information generation portion 140 causes the pattern J1 to reflect the absorption coefficient according to the arrangement of the substances as the information related to the arrangement of the substances. The absorption coefficient of the substances reflected in the pattern J1 is identified from the reference data RM shown in FIG. 5B referenced by the aforementioned ratio acquirement portion 120 in the process of identifying the ratio RT. That is, according to the reference data RM shown in FIG. 5B, in the process of identifying the ratio RT, the types of the substance A and the substance B rendering the ratio RT are identified. If the type of each substance is identified, then the absorption coefficient of that substance is identified.

When the pattern J1 is caused to reflect the substance absorption coefficient, it is necessary to identify a position on the pattern J1. This position can be identified from the tomographic image indicated by the first detection information D1 mentioned before, and the ratio RT obtained by the ratio acquirement portion 120. That is, by comparing the size of the image of each substance shown in the tomographic image indicated by the first detection information D1, and the ratio RT of the substance, it is possible to grasp the relation between the absorption coefficient of each substance rendering the ratio RT, and the position of the substance displayed in the tomographic image. Based on the above relation, the third information generation portion 140 identifies the position on the pattern J1 shown in FIG. 19 to reflect the absorption coefficient of the substances. By virtue of this, the pattern J2 shown in FIG. 19 is obtained. In the example shown in FIG. 19, the absorption coefficient is reflected in the information of the pixel F, whereas the information of the other pixels remains the same as it is.

According to the fourth embodiment, because the second detection information D2 is caused to reflect the absorption coefficient of each substance obtained from the X-ray spectrum data DS, the internal state of the measuring object S is reflected better in the third detection information D3. Therefore, it is possible to have a more detailed knowledge of the internal state of the measuring object S than in the first embodiment. Further, in the fourth embodiment, because the third detection information D3 is generated by the back projection method, it is possible to reduce the load of the image processing for generating the third detection information D3 as compared with the third embodiment using the successive approximation method.

Fifth Embodiment

Next, a fifth embodiment will be explained.

In the following explanation, the same reference numerals will be assigned to the constitutive parts or components which are the same as or equivalent to those of the embodiments described above, and the explanations therefor will be simplified or omitted.

In the fifth embodiment, an explanation will be made on a structure manufacturing system including the X-ray device 1 described above.

Figure 20:
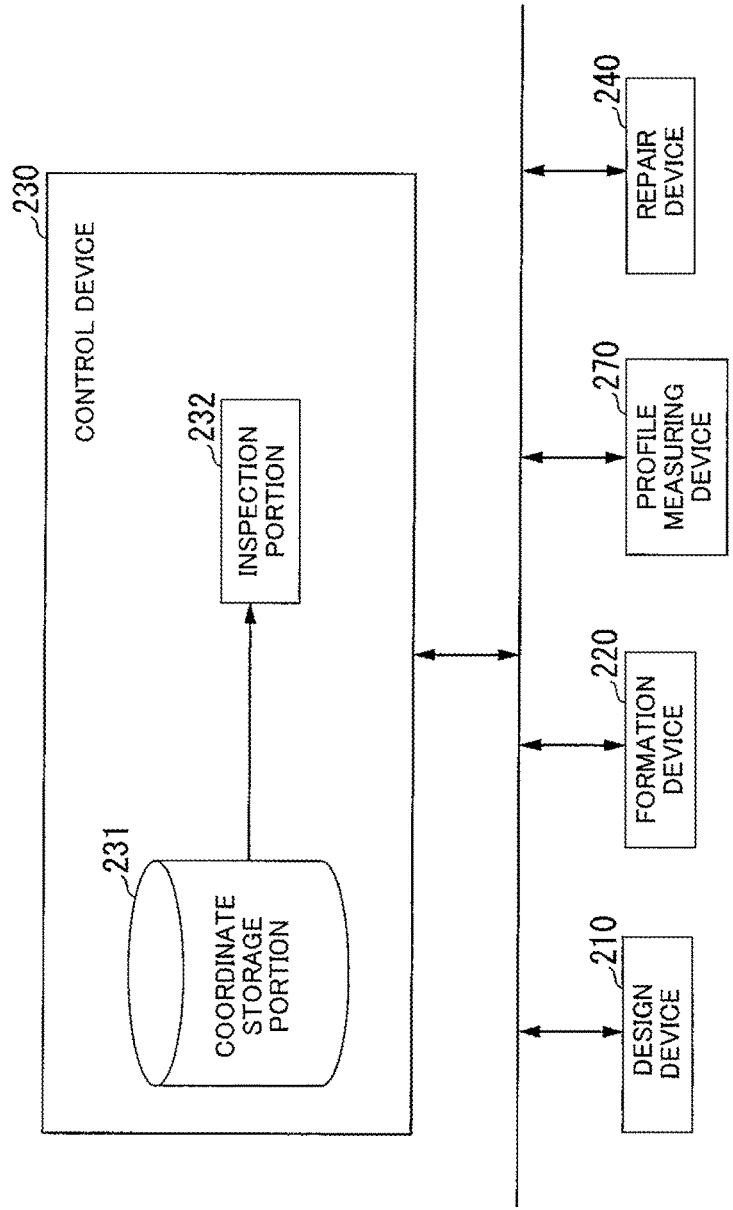
FIG. 20 is a diagram showing an example of a structure manufacturing system including the X-ray device.
Figure 21:
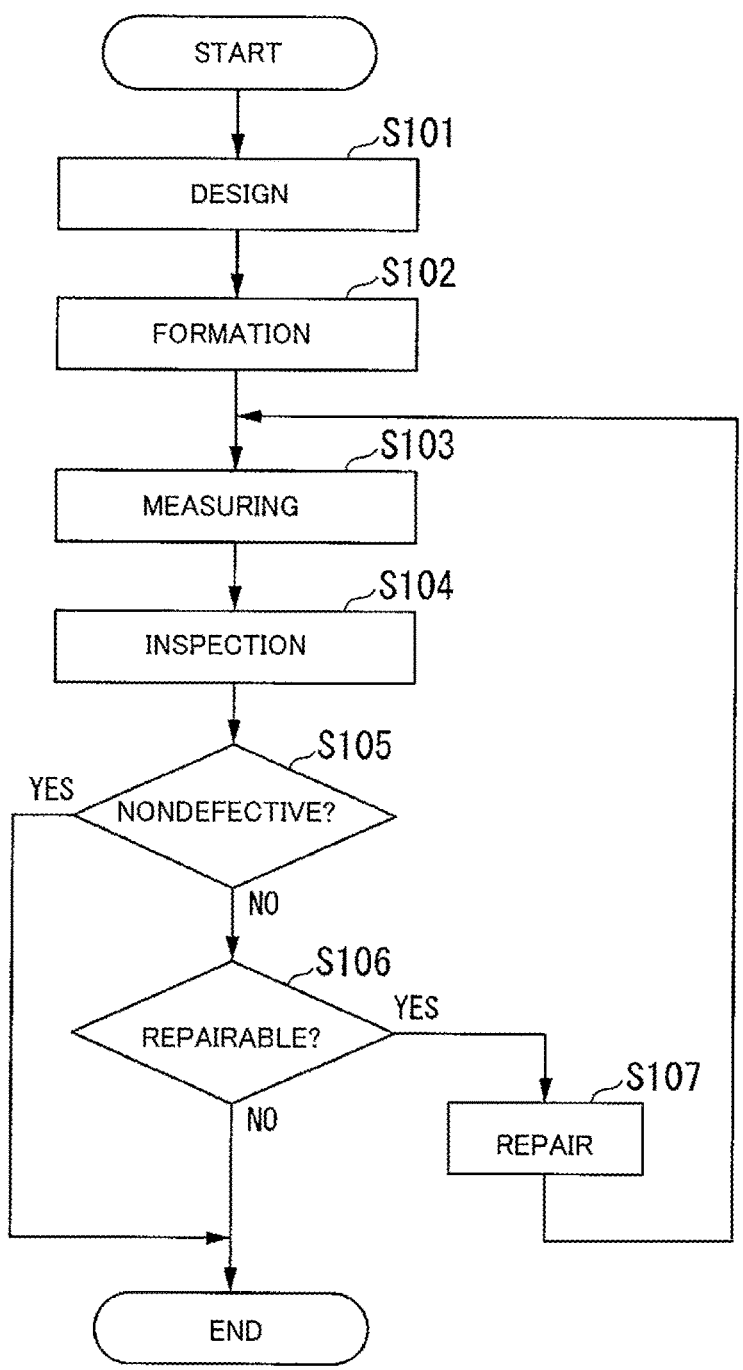
FIG. 21 is a flowchart showing a processing flow according to the structure manufacturing system.

FIG. 20 is a block diagram of configuration of a structure manufacturing system 200. The structure manufacturing system 200 includes a profile measuring device 270 constructed of the X-ray device 1 mentioned above, a design device 210, a formation device 220, a control device (inspection device) 230, and a repair device 240. In the fifth embodiment, the structure manufacturing system 200 manufactures molded components such as automobile door parts, engine components, gear components, electronic components including circuit substrates, etc.

The design device 210 creates design information related to the profile of a structure, and sends the created design information to the formation device 220. Further, the design device 210 causes an aftermentioned coordinate storage portion 231 (a coordinate storage unit, a coordinate storage member, or a coordinate storage mechanism) of the control device 230 to store the created design information. The design information mentioned here refers to information indicating the coordinates of each position of the structure. The formation device 220 fabricates the above structure based on the design information inputted from the design device 210. The formation process of the formation device 220 includes at least one of casting, forging, and cutting.

The X-ray device 1 sends information indicating the measured coordinates to the control device 230. The control device 230 includes the coordinate storage portion 231 and an inspection portion 232 (an inspection unit, an inspection member, or an inspection mechanism). The coordinate storage portion 231 stores the design information from the design device 210. The inspection portion 232 reads out the design information from the coordinate storage portion 231. The inspection portion 232 creates information (profile information) signifying the fabricated structure from the information indicating the coordinates received from the X-ray device 1. The inspection portion 232 compares the information (the profile information) indicating the coordinates received from the profile measuring device 270 with the design information read out from the coordinate storage portion 231. Based on the comparison result, the inspection portion 232 determines whether or not the structure is formed in consistency with the design information. In other words, the inspection portion 232 determines whether or not the fabricated structure is nondefective. If the structure is not formed in consistency with the design information, then the inspection portion 232 determines whether or not it is repairable. If it is repairable, then the inspection portion 232 calculates to specify the defective portions and repairing amount based on the comparison result, and sends information indicating the defective portions and repairing amount to the repair device 240.

Based on the information indicating the defective portions and repairing amount received from the control device 230, the repair device 240 processes the defective portions of the structure.

FIG. 20 is a flowchart showing a processing flow according to the structure manufacturing system 200. First, the design device 210 creates design information related to the profile of a structure (step S101). Next, the formation device 220 fabricates the structure based on the design information (step S102). Then, the X-ray device 1 measures the coordinates with respect to the profile of the structure (step S103). Then, the inspection portion 232 of the control device 230 inspects whether or not the structure is fabricated in consistency with the design information by comparing the created profile information of the structure from the X-ray device 1 with the above design information (step S104).

Next, the inspection portion 232 of the control device 230 determines whether or not the fabricated structure is nondefective (step S105). If the fabricated structure is nondefective (step S106: Yes), then the structure manufacturing system 200 ends the process. On the other hand, if the fabricated structure is defective (step S106: No), then the inspection portion 232 of the control device 230 determines whether or not the fabricated structure is repairable (step S107).

If the fabricated structure is repairable (step S107: Yes), then the repair device 240 reprocesses the structure (step S108), and the process returns to step S103. On the other hand, if the fabricated structure is not repairable (step S107: Yes), then the structure manufacturing system 200 ends the process. With that, the process of the flowchart is ended.

In the above manner, because the X-ray device 1 in the above embodiments can correctly measure the coordinates of the structure, the structure manufacturing system 200 is able to determine whether or not the fabricated structure is nondefective. Further, when the structure is defective, the structure manufacturing system 200 is able to reprocess the structure to repair the same.

While the several embodiments of the present teaching have been explained above in detail with reference to the accompanying drawings, any specific configuration of the present teaching is not limited to those embodiments, but it is possible to apply appropriate modifications thereto without departing from the true spirit and scope of the present teaching. Further, it is possible to appropriately combine the requirements of the respective embodiments described above. Further, there may be some cases of not using some of the components. Further, in so far as permitted by laws and regulations, the present description incorporates, as a part thereof, all the disclosures of the Japanese patent publications and U.S. patents cited in the respective embodiments described above.

It is possible to carry out the process of the X-ray device by recording a program for realizing the function of the X-ray device according to the present teaching into a computer-readable recording medium, and letting a computer system read in the program recorded in the recording medium so as to execute the same. Further, the term "computer system" used here is intended to include an OS (Operating System), and some hardware such as peripheral equipment and the like. Further, the "computer system" is intended to also include a WWW (World Wide Web) system provided with a website provision environment (or a display environment). Further, the term "computer-readable recording medium" refers to a portable medium such as a flexible disk, magnetic optical disk, ROM, CD-ROM, etc., or a storage device such as a hard disk built in the computer system, etc. Further, the "computer-readable recording medium" is intended to also include devices which retain the program for a certain period of time such as volatile memory (RAM) inside the computer system which acts as a server or a client on the occasion of transmitting the program via a network such as the Internet or the like, or via communication lines such as telephone lines or the like.

Further, the abovementioned program may also be transmitted to other computer systems from the computer system having stored this program in its storage device or the like via a transmission medium, or by some transmission wave in the transmission medium. Here, the term "transmission medium" transmitting the program refers to a medium which has such a function of transmitting information as a (communication) network such as the Internet or the like, or communication links (lines) such as telephone lines or the like. Alternatively, the abovementioned program may serve the purpose of realizing part of the aforementioned function. Still alternatively, it may be a so-called difference file (difference program) which enables the realization of the aforementioned function by combination with the program already recorded in the computer system.

In the embodiments mentioned above, while the detection portion 40 detects the intensity $I_0$ of the X-ray irradiating the measuring object S per unit area of a plane orthogonal to the X-ray irradiation direction, and the intensity I of the transmission X-ray transmitted through the measuring object S, the present teaching is not necessarily limited to such a configuration. For example, the detection portion 40 may be configured to detect only the intensity I of the transmission X-ray transmitted through the measuring object S. For example, if it is possible to assume in advance that the intensity of the X-ray irradiating the measuring object S is constant, then it is possible to obtain a substantially equivalent data to the X-ray spectrum data in the foregoing explanations by detecting only the intensity I of the transmission X-ray transmitted through the measuring object S.

In the embodiments mentioned above, if the ratio RT between the first substance and the second substance contained in the measuring object S is known in advance, then the ratio acquirement portion 120 may omit the calculation of the ratio RT based on the X-ray spectrum data DS obtained from the detection portion 42, in this case, the ratio acquirement portion 120 may acquire design information such as CAD data to calculate the ratio RT therefrom. Alternatively, it is possible to receive ratio information entered by a person in charge of the measuring, and calculate the ratio RT based thereon. That is, the ratio acquirement portion 120 may calculate the ratio RT based on either at least one of the X-ray spectrum data DS obtained from the detection portion 42, the design information such as CAD data, and the ratio information entered by the person in charge of the measuring, or an arbitrary combination of those pieces of data and information. In the case of combining a plurality of pieces of information, if there is difference between the respective pieces of information, then it is possible to use an average value thereof. On this occasion, it is possible to adopt a weighted mean value based on the degree of accuracy (error) of each piece of information. Further, it is also possible to individually use a plurality of pieces of information to calculate the ratio RT corresponding to each of them, so as to create second information.

Further, it is not indispensable to acquire the ratio information related to the whole measuring object but, as necessary, it is possible to extract only some ratio information corresponding to part of the measuring object, and use the same as the ratio information. For example, if the ratio acquirement portion 120 acquires the ratio information based on the design information such as CAD data, then it is possible to acquire the substance ratio information in a tomographic image obtained as first information. In this case, it is possible to first specify from what position of the measuring object S is the tomographic image obtained as the first information, and then acquire the substance ratio information at the position corresponding to the tomographic image (or in the vicinity of an area including the position corresponding to the tomographic image). In the case of calculating the ratio RT based on the X-ray spectrum data DS obtained from the detection portion 42, likewise, it is also possible to extract, as necessary, only some ratio information corresponding to part of the measuring object, and use the same as the ratio information.

Further, in the embodiments mentioned above, the first detection information D1 may be changed to the second detection information D2 based on the ratio information not for a three-dimensional image but for a two-dimensional image. In this case, the ratio acquirement portion 120 may also acquire the ratio information by using the design information such as CAD data as described above. In this case, it is possible to extract some ratio information related to the portion corresponding to a projective mapping of the measuring object projected on the two-dimensional image, and use the same as the ratio information.

Further, in the embodiments mentioned above, the place of acquiring the first information, the place of generating the second information, the place of acquiring the ratio information, and the place of generating the frequency distributions need not necessarily be in the same location, but at least one of those places may be in a different location. For example, the place of generating the second information need not be in an information processing device connected to the X-ray device which has obtained the first information in advance, but may be in an information processing device provided independently of that X-ray device. For example, the information processing device may be connected to the detection portion 42 to acquire the ratio information. Further, it is also possible to collect the information acquired respectively in different places into an external information processing device provided independently of the X-ray device via communication lines such as, for example, the Internet, an intranet, etc., and generate the second information in the external information processing device based on that collected information.

Using a spectrometer such as the detection portion 42, it is possible to irradiate the measuring object S with X-ray of continuously changing wavelength, and measure the intensity of the X-ray transmitted through the measuring object S. Alternatively, it is possible to irradiate the measuring object S with X-ray of discretely changing wavelength, and measure the intensity of the X-ray transmitted through the measuring object S. Here, it is possible to either only acquire the intensity of the X-ray of a signal wavelength or collectively acquire the intensities of the X-ray in a predetermined range of wavelengths.

What is claimed is:

1. An X-ray device comprising:
an irradiator configured to irradiate an X-ray to a measuring object;
a detector configured to detect transmission X-ray transmitted through the measuring object; and
a controller connected to the irradiator and the detector, and configured to:
generate first information, based on an image reconstructed from a result of detecting the transmission X-ray, the first information including information of an area in which an absorption coefficient of X-ray detected falls within a first range and information of an area in which an absorption coefficient of X-ray detected falls within a second range that is different from the first range;
acquire ratio information indicating a ratio between a first substance and a second substance included in the measuring object;
based on the ratio information and the first information, generate second information including information of an area which corresponds to the first substance and in which an absorption coefficient of X-ray falls within a third range obtained by merging the first range and the second range, so that a frequency distribution of signal intensity representing the absorption coefficient within the first range and the absorption coefficient within the second range is reconstructed to a frequency distribution of signal intensity representing the absorption coefficient within the third range; and
generate a modified image in which an area corresponding to the first substance is determined based on the second information.

2. The X-ray device according to claim 1, wherein the controller is configured to define a plurality of divided section by dividing a virtual space corresponding to a space including at least part of the measuring object, and
wherein the controller is further configured to generate the first information based on a second image reconstructed from a result of detecting a plurality of transmission X-rays for which the X-rays have respectively different incident directions on the measuring object, and wherein a value according to the first or second absorption coefficient is allocated to each of the plurality of divided sections.

3. The X-ray device according to claim 2, wherein the controller is further configured to generate the second information in which a distribution of the number of the plurality of divided sections in the first information has a mode value associated with the highest frequency, and a half-value width with respect to the mode value in the first information is narrowed.

4. The X-ray device according to claim 3, wherein the controller is further configured to generate the second information in which the value according to the first absorption coefficient of the first substance is included in a predetermined range of a frequency distribution centered at the value allocated to the divided section with the mode value in the first information, and any value included in the predetermined range is changed into the value according to the absorption coefficient of the first substance.

5. The X-ray device according to claim 4, wherein the controller is further configured to generate some divided sections arranged around the divided sections to which the value is allocated according to the absorption coefficient of the first substance in the first information, and the value of the extracted divided sections is changed into the value according to the absorption coefficient of the first substance.

6. The X-ray device according to claim 3, wherein the distribution of the number of the divided sections in the first information has a plurality of predetermined ranges, and each of the plurality of predetermined ranges has a mode value.

7. The X-ray device according to claim 2, wherein the controller is further configured to generate the second information in which with respect to portions of different values of adjacent divided sections in the first information, one value of the different portions is made to be equal to the other value, so as to equalize the values of the adjacent divided sections.

8. The X-ray device according to claim 2, wherein the detector is further configured to detect intensity of the X-ray transmitted through the measuring object according to a wavelength of the X-ray, and wherein the controller is further configured to use a signal of a detection position to generate the ratio between the first substance and the second substance.

9. The X-ray device according to claim 8, wherein the detector is further configured to measure a ratio between intensity of the X-ray irradiating the measuring object, and the intensity of the X-ray transmitted through the measuring object, according to the wavelength of the X-ray.

10. The X-ray device according to claim 8, wherein the ratio information of the measuring object is generated by using a storage portion storing a reference data indicating the signal of the detector when the detector has detected each of the first substance and the second substance.

11. The X-ray device according to claim 2, wherein the controller is further configured to acquire the ratio information from design information of the measuring object.

12. The X-ray device according to claim 2, wherein the controller is further configured to acquire the ratio information indicating a volume ratio between the first substance and the second substance contained in the measuring object.

13. The X-ray device according to claim 2, wherein the controller is further configured to generate third information with the second information as an initial value by a successive approximation method.

14. The X-ray device according to claim 2, wherein the controller is further configured to generate third information with the second information as an initial value by a back projection method.

15. A method for acquiring information related to a structure of a measuring object by irradiating the measuring object with X-ray, the method comprising:
irradiating the measuring object with the X-ray, and detecting transmission X-ray transmitted through the measuring object;
generating first information, based on an image reconstructed from a result of detecting the transmission X-ray, the first information including information of an area in which an absorption coefficient of X-ray detected falls within a first range and information of an area in which an absorption coefficient of X-ray detected falls within a second range that is different from the first range;

acquiring ratio information indicating a ratio between a first substance and a second substance included in the measuring object;

based on the ratio information and the first information, generating second information including information of an area which corresponds to the first substance and in which an absorption coefficient of X-ray falls within a third range obtained by merging the first range and the second range, so that a frequency distribution of signal intensity representing the absorption coefficient within the first range and the absorption coefficient within the second range is reconstructed to a frequency distribution of signal intensity representing the absorption coefficient within the third range; and generating a modified image in which an area corresponding to the first substance is determined based on the second information.

16. A structure manufacturing method, comprising:

creating design information with respect to a profile of a structure;

fabricating the structure based on the design information;

measuring the profile of the fabricated structure by using the X-ray device according to claim 2; and comparing information of the profile obtained in the measuring with the design information.

17. The structure manufacturing method according to claim 16, further comprising repairing the structure based on a comparison result of the inspection to reprocess the structure.

18. The structure manufacturing method according to claim 17, wherein the repairing the structure is carrying out fabricating the structure over again.

19. A non-transitory computer-readable recording medium storing a computer program configured to cause a computer connected to an X-ray device to carry out a control of the X-ray device, the computer program comprising instructions for controlling the X-ray device to carry out:

irradiating a measuring object with X-ray, and detecting transmission X-ray transmitted through the measuring object;

generating first information, based on an image reconstructed from a result of detecting the transmission X-ray, the first information including information of an area in which an absorption coefficient of X-ray detected falls within a first range and information of an area in which an absorption coefficient of X-ray detected falls within a second range that is different from the first range;

acquiring ratio information indicating a ratio between a first substance and a second substance included in the measuring object;

based on the ratio information and the first information, generating second information including information of an area which corresponds to the first substance and in which an absorption coefficient of X-ray falls within a third range obtained by merging the first range and the second range, so that a frequency distribution of signal intensity representing the absorption coefficient within the first range and the absorption coefficient within the second range is reconstructed to a frequency distribution of signal intensity representing the absorption coefficient within the third range; and generating a modified image in which an area corresponding to the first substance is determined based on the second information.

20. The X-ray device according to claim 2, wherein the second information generation portion is configured to generate the second information in which a value allocated to one of the divided sections in the first information is decreased.

21. The method according to claim 15, wherein the first information is generated based on a second image reconstructed from a result of detecting a plurality of transmission X-rays for which the X-rays have respectively different incident directions on the measuring object.

22. The non-transitory computer-readable recording medium according to claim 19, wherein the first information is generated based on a second image reconstructed from a result of detecting a plurality of transmission X-rays for which the X-rays have respectively different incident directions on the measuring object.

23. The X-ray device according to claim 1, wherein the controller is configured to define a plurality of divided section by dividing a virtual space corresponding to a space including at least part of the measuring object, and wherein the controller is further configured to generate frequency information of first information in which a value according to a first or second absorption coefficient is allocated to each of the plurality of divided sections, wherein the allocated value indicates a number of the divided sections according to magnitude of the allocated value in the first information.

24. The method according to claim 15, further comprising:

defining a plurality of divided section by dividing a virtual space corresponding to a space including at least part of the measuring object, and generating frequency information of first information in which a value according to a first or second absorption coefficient is allocated to each of the plurality of divided sections, wherein the allocated value indicates a number of the divided sections according to magnitude of the allocated value in the first information.

25. The non-transitory computer-readable recording medium according to claim 19, wherein the computer program further comprises instructions for controlling the X-ray device to carry out:

defining a plurality of divided section by dividing a virtual space corresponding to a space including at least part of the measuring object, and generating frequency information of first information in which a value according to a first or second absorption coefficient is allocated to each of the plurality of divided sections, wherein the allocated value indicates a number of the divided sections according to magnitude of the allocated value in the first information.

* * * * *